United States Patent [19]

Panoz et al.

[11] Patent Number: 4,863,742
[45] Date of Patent: Sep. 5, 1989

[54] CONTROLLED ABSORPTION PHARMACEUTICAL COMPOSITION

[75] Inventors: Donald E. Panoz, Tuckerstown, Bermuda; Edward J. Geoghegan, Westmeath, Ireland

[73] Assignee: Elan Corporation PLC, Athlone, Ireland

[21] Appl. No.: 64,765

[22] Filed: Jun. 19, 1987

[30] Foreign Application Priority Data

Jun. 20, 1986 [IE] Ireland ............................... 1661/86

[51] Int. Cl.$^4$ ............................................. A61K 9/24
[52] U.S. Cl. ..................... 424/473; 424/471; 424/472
[58] Field of Search ............... 424/471–473; 514/781

[56] References Cited

U.S. PATENT DOCUMENTS 4,461,759 7/1984 Dunn ........................... 424/469 X
4,606,909 8/1986 Bechgaard et al. ................ 424/469

FOREIGN PATENT DOCUMENTS 63266 10/1982 European Pat. Off. .
122077 10/1984 European Pat. Off. .
123470 10/1984 European Pat. Off. .
156077 10/1985 European Pat. Off. .

OTHER PUBLICATIONS

*Pharmaceutical Composition*, Patents Act, 1964, pp. 1–15, BASF Aktiengesellschaft, Fed Rep of German, published 11-3-1982.

*Primary Examiner*—Michael Lusigman
*Attorney, Agent, or Firm*—Robert Hardy Falk; Marla J. Church

[57] ABSTRACT

A controlled absorption verapamil containing pellet formulation for oral adminstration comprises a core of a powder mixture containing verapamil or a pharmaceutically acceptable salt thereof and an organic acid and a polymeric material, said core comprising layers of said powder mixture and said polymeric material superimposed one upon the other and said polymeric material being present in an amount effective to ensure that all of said powder mixture is coated into said core and a multi-layer membrane surrounding said core, the number of layers in said membrane and the ratio of the various polymers comprising the membrane being effective to permit release of the verapamil from the pellet at a rate allowing controlled absorption thereof over a 24 hour period following oral administration, said rate being measured in vivo and having a Tmax between 6 and 16 hours.

38 Claims, 9 Drawing Sheets

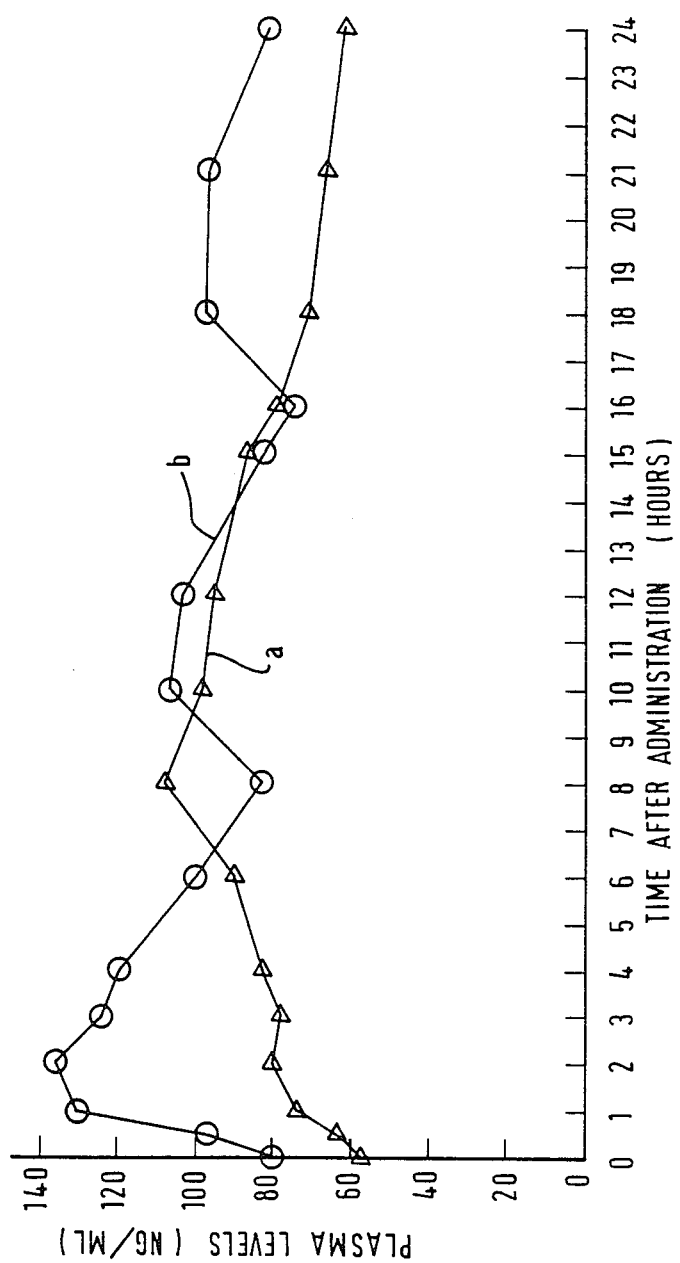

CONTROLLED ABSORPTION PHARMACEUTICAL COMPOSITION

BACKGROUND OF THE INVENTION

This invention relates to a verapamil pellet formulation for oral administration and the use thereof in the preparation of verapamil-containing pharmaceutical formulations which allow one to achieve a controlled absorption of verapamil in vivo. The invention relates, in particular, to a verapamil formulation suitable for once daily administration.

DESCRIPTION OF THE PRIOR ART

Verapamil (δ-[N-(3,4-dimethoxyphenethyl)-N-methylamino]-α-(3,4-dimethoxyphenethyl)-α-isopropylvaleronitrile) decreases the oxygen requirements of the myocardium and also reduces the work load of the heart by diminishing peripheral resistance. Verapamil hydrochloride is used in the prophylaxis and treatment of angina of effort in doses of 40 to 80 mg thrice daily by mouth according to the severity of the condition. It is also used by slow intravenous injection in doses of 5 mg up to thrice daily in severe angina of effort not responsive to oral therapy. Verapamil is also used in the treatment of hypertension. Verapamil hydrochloride is sold under the Trade Mark "Cordilox" as 2-ml ampoules of an injection containing 2.5 mg per ml, for intravenous use, and as tablets of 40 mg.

EP-A No. 0 063 266 describes a sustained release form of verapamil which it is stated allows the frequency of administration to be reduced to once or twice daily. The formulation contains a rapid release form of verapamil and a sustained (slow) release form of verapamil in a ratio of 1:0.6 to 1:6. No data is presented in the Specification of EP-A No. 0 063 266 demonstrating in vivo plasma concentration levels following administration.

It is an object of the present invention to provide a controlled absorption form of verapamil which is suitable for once daily administration, which is characterised by a high degree of absorption, which is substantially invariable from subject to subject, and by significant plasma levels of verapamil which are maintained for an extended period after administration.

SUMMARY OF THE INVENTION

Accordingly, the invention provides a controlled absorption verapamil containing pellet formulation for oral administration, said pellet comprising:
  (i) a core of
     (a) a powder mixture containing verapamil or a pharmaceutically acceptable salt thereof and an organic acid selected from adipic acid, ascorbic acid, citric acid, fumaric acid, malic acid, succinic acid and tartaric acid or a mixture thereof, and
     (b) a polymeric material containing a major proportion of a pharmaceutically acceptable water soluble polymer and a minor proportion of a pharmaceutically acceptable water insoluble polymer, said core comprising layers of said powder mixture and said polymeric material superimposed one upon the other and said polymeric material being present in an amount effective to ensure that all of said powder mixture is coated into said core; and
  (ii) a multi-layer membrane surrounding said core and containing a major proportion of a pharmaceutically acceptable film-forming, water-insoluble polymer and a minor proportion of a pharmaceutically acceptable film-forming, water-soluble polymer,
the number of layers in said membrane and the ratio of said water-soluble polymers to said water-insoluble polymers being effective to permit release of said verapamil from said pellet at a rate allowing controlled absorption thereof over a 24 hour period following oral administration, said rate being measured in vivo and having a Tmax between 6 and 16 hours.

DETAILED DESCRIPTION OF THE INVENTION

Preferably, the pellet formulation according to the invention has a Tmax in vivo between 7 and 10 hours.

The invention also provides a controlled absorption verapamil containing pellet formulation for oral administration, said pellet comprising:
  (i) a core of
     (a) a powder mixture containing verapamil or a pharmaceutically acceptable salt thereof and an organic acid selected from adipic acid, ascorbic acid, citric acid, fumaric acid, malic acid, succinic acid and tartaric acid or a mixture thereof, and
     (b) a polymeric material containing a major proportion of a pharmaceutically acceptable water soluble polymer and a minor proportion of a pharmaceutically acceptable water insoluble polymer,
     said core comprising layers of said powder mixture and said polymeric material superimposed one upon the other and said polymeric material being present in an amount effective to ensure that all of said powder mixture is coated into said core; and
  (ii) a multi-layer membrane surrounding said core and containing a major proportion of a pharmaceutically acceptable film-forming, water-insoluble polymer and a minor proportion of a pharmaceutically acceptable film-forming, water-soluble polymer,
the number of layers in said membrane and the ratio of said water-soluble polymers to said water-insoluble polymers being effective to permit release of said verapamil from said pellet at a rate allowing controlled absorption thereof over a 24 hour period following oral administration, said rate being measured in vitro as a dissolution rate of said pellet in a potassium chloride medium which, when measured in a basket assembly according to U.S. Pharmacopoeia XXI at 37° C., substantially corresponds to the following:
  (a) from 0 to 25% of the total verapamil is released after one hour of measurement in said assembly;
  (b) from 0 to 35% of the total verapamil is released after four hours of measurement in said assembly;
  (c) from 30 to 60% of the total verapamil is released after a total of eight hours of measurement in said assembly;
  (d) from 50 to 75% of the total verapamil is released after eleven hours of measurement in said assembly; and
  (e) not less than 80% of the total verapamil is released after twenty-four hours of measurement in said assembly.

More particularly, the potassium chloride medium is a medium as defined in Example 1.

Verapamil is widely used in anti-anginal therapy and where the patient for one reason or another (for example, takes the dose later than due, is switching from conventional frequently administered immediately released products, etc.) the patient may require a rapid attainment of effective therapeutic blood levels for fast relief of onset of anginal attack.

Accordingly, the invention further provides a controlled absorption verapamil formulation for oral administration comprising a blend of pellets as hereinbefore specified in admixture with pellets of a rapid release form of verapamil to ensure a rapid attainment of effective therapeutic blood levels of verapamil within one hour following administration, said rapid release pellets comprising pellets as hereinbefore specified without said multi-layer membrane, the formulation having a dissolution rate which is substantially pH independent and which when measured in a basket assembly according to U.S. Pharmacopoeia XXI at 37° C. has the following characteristics:

(a) from 10 to 25% of the total verapamil after one hour of measurement in said assembly;
(b) from 20 to 35% of the total verapamil is released after four hours of measurement in said assembly;
(c) from 35 to 60% of the total verapamil is released after eight hours of measurement in said assembly;
(d) from 50 to 75% of the total verapamil is released assembly; and
(e) not less than 80% of the total verapamil is released after twenty-four hours of measurement in said assembly.

Preferably, the verapamil is in the form of a pharmaceutically acceptable salt thereof, more particularly the hydrochloride salt thereof.

The verapamil component and organic acid are preferably present in a ratio of from 1:1 to 10:1.

As used herein the term water-soluble polymer is intended to include polymers which are freely water permeable and porous polymers. The term water-insoluble polymer as used herein is intended to include polymers which are slightly water permeable or water impermeable and nonporous polymers.

The polymeric material may consist solely of a water soluble polymer or a polymer which is freely permeable to verapamil and water. Alternatively, the polymeric material of the core may include a minor proportion of a water insoluble polymer or a polymer which is slightly permeable to verapamil and water. The ratio of water soluble/freely permeable to water insoluble/slightly permeable polymer is determined by the particular combination of polymers selected.

The water soluble polymer is suitably hydroxypropylmethylcellulose or polyvinylpyrrolidone.

A suitable polymer which is freely permeable to verapamil and water is a polymer sold under the Trade Mark EUDRAGIT RL.

The water insoluble polymer is suitably a cellulose ether such as methyl-, ethyl- or propylcellulose or shellac.

A suitable polymer which is slightly permeable to verapamil and water is a polymer sold under the Trade Mark EUDRAGIT RS.

EUDRAGIT polymers are polymeric lacquer substances based on acrylates and/or methacrylates.

Polymeric materials sold under the Trade Marks EUDRAGIT RL and RS are acrylic resins comprising copolymers of acrylic and methacrylic acid esters with a low content of quaternary ammonium groups and are described in the "EUDRAGIT" brochure of Messrs. Rohm and Haas (1985) wherein detailed physical-chemical data of these products is given. The ammonium groups are present as salts and give rise to the permeability of the lacquer films. EUDRAGIT RL and RS are freely permeable (RL) or slightly permeable (RS), respectively, independent of pH.

The core suitably has between 20 and 120 layers of the core-forming materials and is built up in a manner known per se.

Preferably, the multi-layer arrangement of verapamil, organic acid and polymeric material is built up on a central inert core suitably consisting of a non-pareil seed of sugar or starch having an average diameter in the range of 0.3–0.7 mm, especially 0.4–0.5 mm, in a conventional coating pan.

The core may also include other components such as a lubricant, a dispersing agent or a surfactant. A suitable and particularly preferred lubricant is talc and a suitable surfactant is sodium lauryl sulphate.

The verapamil or pharmaceutically acceptable salt thereof, organic acid and optionally other components such as a lubricant are blended to form a homongenous powder. The blend is suitably passed through a No. 100 mesh screen using a milling machine. Alternate layers of a coating solution/suspension of the polymeric material and the powder are applied to the central inert core so as to build up the multi-layer arrangement of the active core. The coating solution/suspension of the polymeric material comprises one or more polymers dissolved/suspended in a suitable solvent or mixture of solvents. The concentration of the polymeric material in the coating solution/suspension is determined by the viscosity of the final solution. A suitable plasticizer such as diethylphthalate may be added to the coating solution/suspension. Especially preferred coating solutions/suspensions include:

(a) 10% polyvinylpyrrolidone in isopropanol or ethanol;
(b) 5% hydroxypropylmethylcellulose in methanol/methylene chloride 60/40; and
(c) 5% EUDRAGIT RL in isopropanol/acetone 60/40;

The membrane of the film-forming polymer or mixture of polymers surrounding the core has a major proportion of a water insoluble polymer and a minor proportion of a water soluble polymer as hereinbefore defined, the ratio of water insoluble to water soluble polymer being determined by the inherent solubility characteristics of the polymers selected.

Suitable combinations of water insoluble and water soluble polymers for the membrane include: ethylcellulose and hydroxypropylmethylcellulose in a ratio of from 7:1 to 9:3; shellac and polyvinylpyrrolidone in the ratio of from 8:0.5 to 9.5:2; and cellulose acetate and polyvinylalcohol in a ratio of from 7:1 to 9:3.

The membrane may also be composed of a major proportion of a non-porous polymer and a minor proportion of a porous polymer, the ratio of non-porous to porous polymer being determined by the inherent porosity of the respective polymers.

Examples of porous polymers include polyvinylpyrrolidone, Eudragit RL, polyvinylalcohol and hydroxypropylmethylcellulose. Examples of non-porous polymers include Eudragit RS, methyl-, ethyl- or propyl cellulose and shellac.

The membrane may further be composed of a major proportion of a polymer which is slightly permeable to verapamil and water and a minor proportion of a polymer which is freely permeable to verapamil and water, the ratio of slightly permeable to freely permeable polymer being determined by the inherent permeability of the respective polymers. A suitable combination of a polymer which is slightly permeable to verapamil and water and a polymer which is freely permeable to verapamil and water is EUDRAGIT RS and EUDRAGIT RL in a ratio of from 7.5:0.5 to 9.5:2.5.

The membrane is built up by applying a plurality of coats of membrane polymer solution or suspension to the core as hereinafter described. The membrane solution or suspension contains the polymer(s) dissolved or suspended, respectively, in a suitable solvent or mixture of solvents, optionally in the presence of a lubricant.

Suitable lubricants are talc, stearic acid and magnesium stearate. A preferred lubricant is talc in an amount of 5% by weight. Preferably, the number of coats of membrane solution or suspension applied is between 8 and 30 coats. Further, preferably, 2–25 ml of membrane solution or suspension is kilogram of cores. The membrane solution or suspension may include a suitable plasticizer such as diethylphthalate.

Especially preferred membrane suspensions include:
(a) 0.5 to 2 parts by volume 10% polyvinylpyrrolidone in isopropanol or ethanol,
  0 8 to 9.5 parts by volume 17.5% shellac in ethanol, and
  5 parts by weight talc;
(b) 0.5 to 2.5 parts by volume 5% EUDRAGIT RL in isopropanol/acetone 60/40,
  7.5 to 9.5 parts by volume 5% EUDRAGIT RS in isopropanol/acetone 60/40, and
  5 parts by weight talc;
(c) 1 to 3 parts by volume hydroxypropylmethylcellulose in methanol/methylene chloride 60/40,
  7 to 9 parts by volume ethylcellulose in methanol/methylene chloride 60/40,
  5 parts by weight talc, and
(d) 1 to 3 parts by volume 10% polyvinylalcohol in ethanol,
  7 to 9 parts by volume 10% cellulose acetate in acetone/isopropanol 50/50,
  5 parts by weight talc.

The pellets may be filled into hard or soft gelatine capsules. The pellets may also be compressed into tablets using a binder and/or hardening agent commonly employed in tableting such as microcrystalline cellulose sold under the Trade Mark "AVICEL" or a co-crystallised powder of highly modified dextrins (3% by weight) and sucrose sold under the Trade Mark "DI-PAC", in such a way that the specific dissolution rate of the pellets is maintained.

The invention also provides a method of treating or controlling blood pressure in a subject suffering from mild to moderate hypertension, comprising administering to said subject on a once per day basis a dose effective to lower the blood pressure of said subject, of a verapamil-containing controlled absorption formulation comprising a first component formulated to provide an effective blood pressure lowering amount of verapamil within one hour following administration and a second component formulated to provide a maximum blood pressure lowering effect within 6 to 16 hours following administration.

The invention additionally provides a method of controlling or preventing angina attacks or reducing the incidence of angina attacks in a subject suffering from angina pectoris, comprising administering to said subject on a once per day basis a dose effective to improve the blood supply and hence increase the oxygen supply to the myocardium of said subject, of a verapamil-containing controlled absorption formulation comprising a first component formulated to provide an amount of verapamil effective to increase the oxygen supply to the myocardium within one hour following administration and a second component formulated to provide a maximum supply of oxygen to the myocardium within 6 to 16 hours following administration.

DESCRIPTION OF THE DRAWINGS

In the accompanying drawings:

FIG. 9 is a graph of plasma levels (ng/ml) of norverapamil at day 9 of adminstration versus time after administration (hours) for verapamil capsules as prepared in Example 2 (curve a) compared with conventional tablets (curve b).

Figure 1:
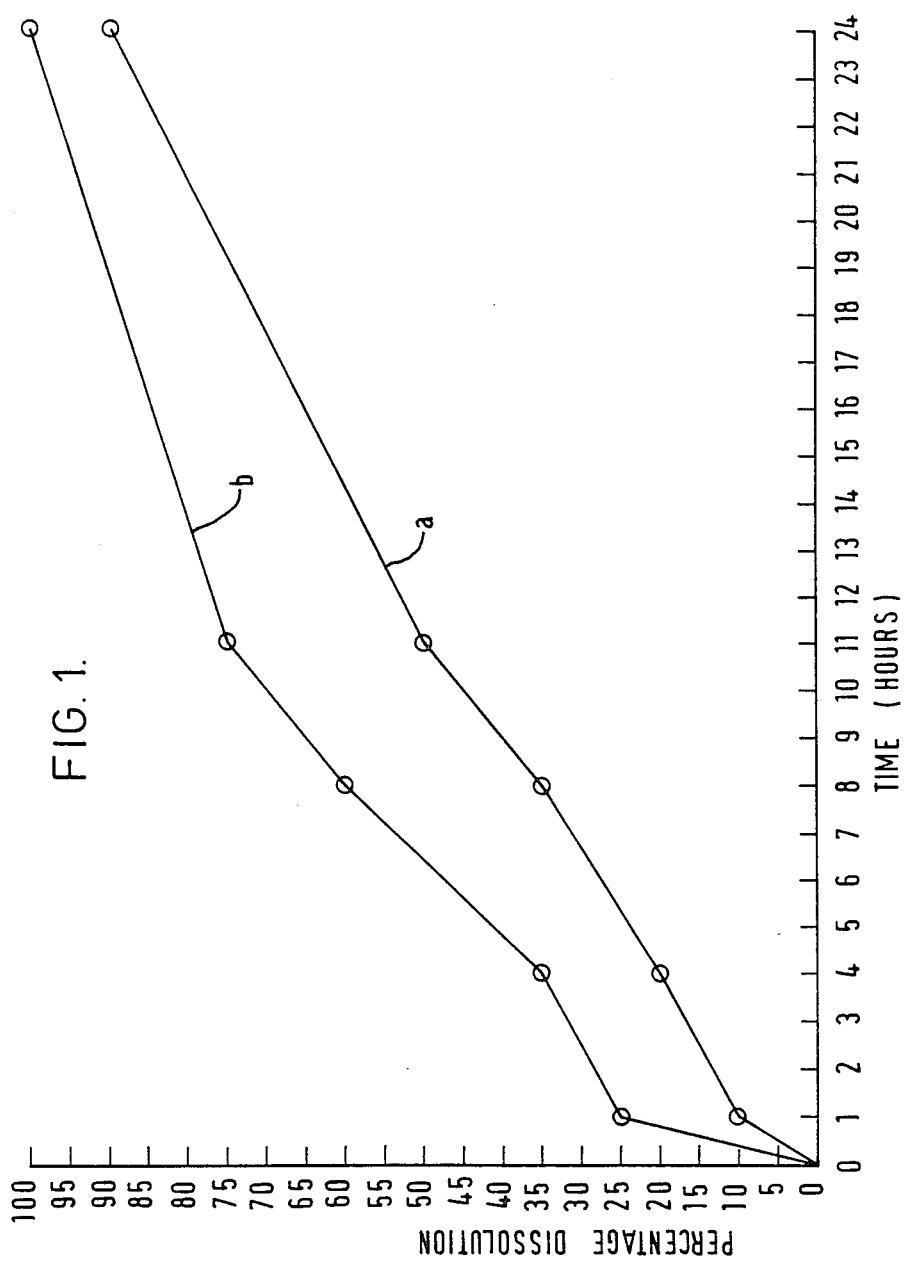
FIG. 1 is a graphic representation of the dissolution rates at pH 7.5 of slow release pellets (curve a) and rapid release pellets (curve b) as prepared in Example 1.

The invention will be further illustrated by the following Examples.

EXAMPLE 1

Verapamil hydrochloride (30 kg), malic acid (10 kg) and talc (2.4 kg) were blended and passed through a No. 100 mesh screen using a conventional milling machine.

A polymer suspension was prepared containing 5% hydroxypropylmethylcellulose in methanol/methylene chloride 60/40.

Sugar/starch seeds (0.4 to 0.5 mm) (9 kg) were placed in a standard coating pan and rotation commenced.

The seeds were wetted with sufficient polymer suspension to dampen them thoroughly and then an amount of the powder blend was dusted on until no more adhered. This step was repeated until all of the powder blend had been applied. The coated seeds were allowed to dry after each application of polymer suspension. When all of the powder had been applied the coated seeds were dried at 40°-60° C. until all of the solvent had been driven off.

A membrane suspension was prepared from the following components:

2 parts by volume 5% hydroxypropylmethylcellulose in methanol/methylene chloride 60/40;

8 parts by volume 5% ethylcellulose in methanol/methylene chloride 60/40;

5 parts by weight talc.

The coated seeds prepared above and which define the active core of the pellets being prepared were placed in a coating pan and rotation commenced. The membrane suspension was applied to the coated seeds in separate coats, each coat corresponding to 10 ml of the membrane suspension per kg of coated seeds. After each coat had been applied the pellets were air dried in the coating pan.

After the final coat had been applied the pellets were dried at 40°-60° C. to evaporate all traces of solvent.

The finished pellets were then subjected to a dissolution test as follows:

Apparatus basket assembly described in U.S.P. XXI at 37° C. and 75 r.p.m.

Medium 7.5 solution (25 ml of 2.0 M potassium chloride plus 950 ml water adjusted to pH 7.5 with sodium hydroxid and to 1000 ml with water).

Method 2 g of pellets were placed in the basket and the test commenced. 1 ml of medium was removed at the specified time points and diluted to 50 ml with 0.1N hydrochloric acid. The absorbance of this solution was read at 279 nm. The absorbance equivalent to 100% dissolution was determined by dissolving 200 mg of ground pellets in sufficient 0.1N hydrochloric acid to produce 100 ml. 1 ml of this solution was diluted to 50 ml with 0.1N hydrochloric acid and its absorbance determined at 279 nm.

The percentage dissolution at each sampling time was calculated by dividing the absorbance of that sample by the 100% absorbance reading.

The dissolution should be in the following range:

| Time (h) | Dissolution (%) |
| --- | --- |
| 1 | 0–25 |
| 4 | 0–35 |
| 8 | 30–60 |
| 11 | 50–75 |
| 24 | Not less than 80 |

Application of coats of the membrane suspension is continued until the desired dissolution pattern is obtained. Pellets with a dissolution pattern within the above range correspond to slow release pellets for use in the controlled absorption pharmaceutical formulation of the invention.

Rapid release pellets as used in the controlled absorption pharmaceutical formulation of the invention are prepared by forming active cores without the subsequent application of a membrane thereto. The dissolution of these rapid release pellets is determined in the manner outlined above but sampling after only one hour, when the dissolution should be greater than 90%.

The slow release and rapid release pellets are then combined in suitable proportions to produce a blend which has a dissolution rate which falls within the following range:

| Time (h) | Dissolution (%) |
| --- | --- |
| 1 | 10–25 |
| 4 | 20–35 |
| 8 | 35–60 |
| 11 | 50–75 |
| 24 | Not less than 80 |

Figure 2:
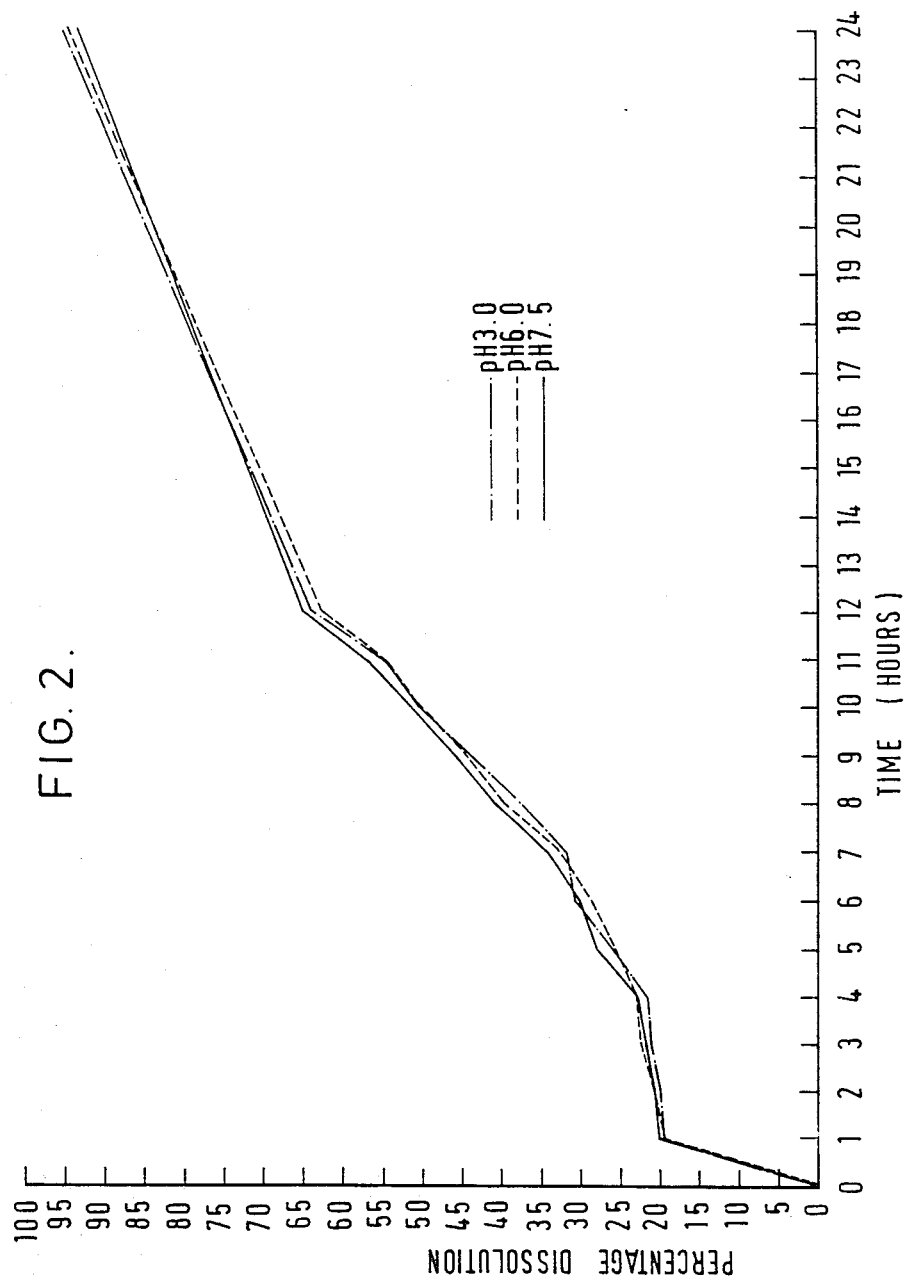
FIG. 2 is a graphic representation of the dissolution rates at pH 3.0, 6.0 and 7.5 for a blend of pellets as prepared in Example 1.

A graphic representation of the dissolution rates of the rapid release pellets and the slow release pellets at pH 7.5 is depicted in FIG. 1 wherein curve a corresponds to the slow release pellets and curve b corresponds to the rapid release pellets. Dissolution rates for a blend of the rapid and slow release pellets were also determined at pH 3.0, pH 6.0 and pH 7.5. The pH 3.0 and 6.0 buffers were prepared as for the buffer of pH 7.5 using hydrochloric acid or sodium hydroxide, as necessary, to adjust the pH. The results are shown in Table 1 and are represented graphically in FIG. 2.

A blend of the rapid and slow release pellets having the desired in vitro dissolution rates was filled into hard gelatine capsules.

EXAMPLE 2

Example 1 was repeated except that malic acid was replaced as the organic acid by fumaric acid (15 kg). Also hydroxypropylmethylcellulose was replaced by 10% polyvinylpyrrolidone in ethanol as the polymer suspension.

The membrane suspension was prepared from the following components:

1 part by volume 10% polyvinylpyrrolidone in ethanol;

9 parts by volume 17.5% shellac in ethanol;

5 parts by weight talc.

Figure 3:
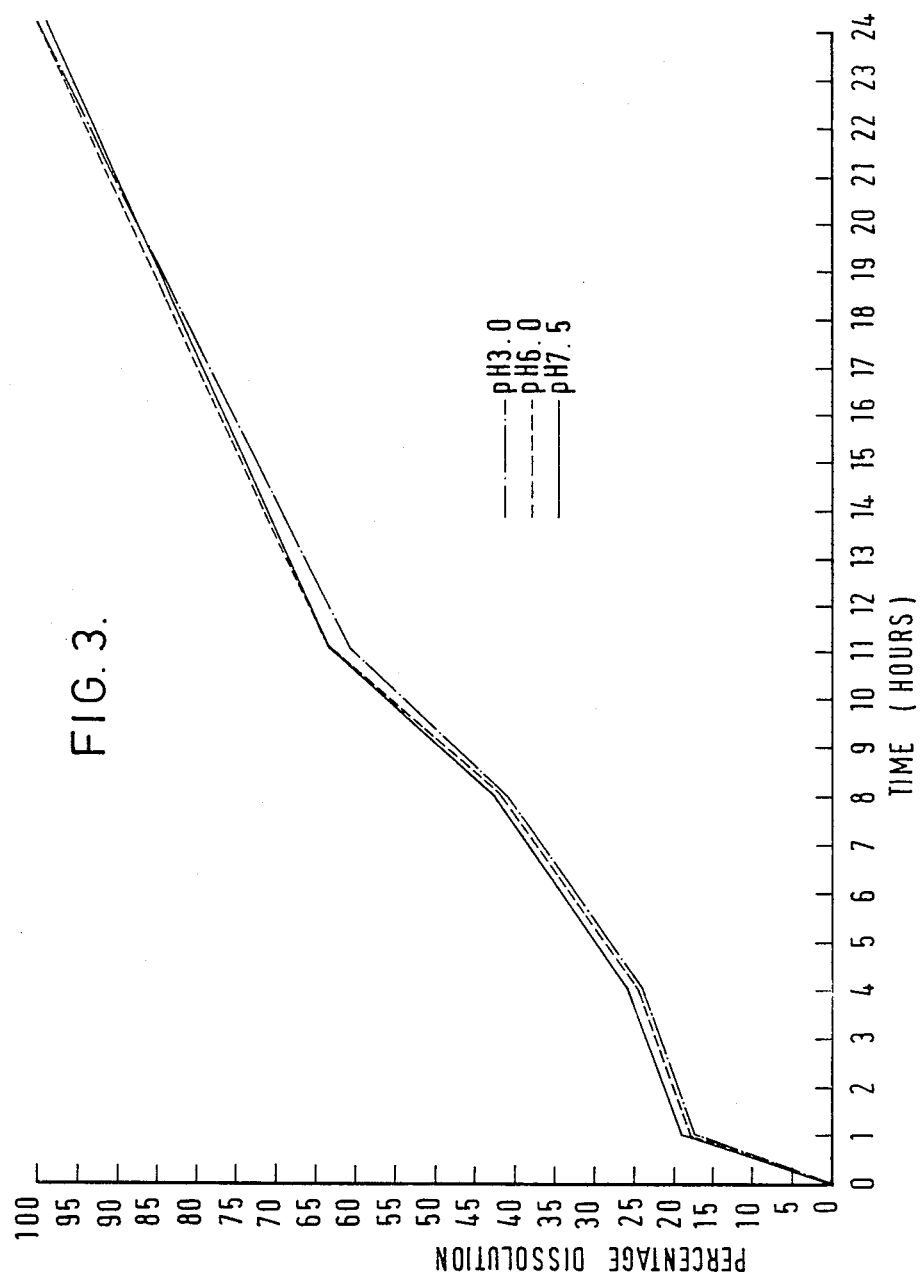
FIG. 3 is a graphic representation of the dissolution rates at pH 3.0, 6.0 and 7.5 for a blend of pellets as prepared in Example 2.

Dissolution tests were carried out as in the case of Example 1 at pH 3.0, 6.0 and 7.5 and the results are given in Table 2. A graphic representation of the results is indicated in FIG. 3.

A blend of the rapid and slow release pellets having the desired in vitro dissolution rates was filled into hard gelatine capsules.

PHARMACOLOGICAL DATA FOR THE VERAPAMIL FORMULATION PREPARED IN EXAMPLE 1

As will be observed from the data given in Tables 3–10 and as represented graphically in FIGS. 4–9, a 240 mg single-dose of a blend of pellets as prepared in Example 1 in capsule form had an equivalent plasma verapamil (Tables 3 and 4) and norverapamil (Tables 5 and 6) level area under the curve (AUC) (1057 and 1580 ng×h/ml, respectively) as conventional Cordilox (Cordilox is a Trade Mark) tablets (Tables 7–10) given as 80 mg at 0, 8 and 16 hours (1099 and 1323 ng×h/ml, respectively). Norverapamil is an active metabolite of verapamil.

The blend of pellets as prepared in Example 1 showed a peak plasma verapamil level (90.1 ng/ml) (Table 4) at 8 hours and a peak norverapamil level (83.9 mg/ml) (Table 6) at 9.4 hours. In contrast Cordilox is rapidly absorbed with an initial peak verapamil level (123.6 ng/ml) (Table 8) and norverapamil (101.1 ng/ml) (Table 10) occurring at 0.64 hours.

In terms of variability, the verapamil formulation of Example 1 was similar to Cordilox tablets: AUC variability for the verapamil formulation of Example 1 has % CV (coefficient of variation)=39.3 for verapamil levels and % CV=35.9 for norverapamil levels. The AUC variability for Cordilox tablets has % CV=41.5 for verapamil levels and % CV=33.5 for norverapamil levels.

Figure 4:
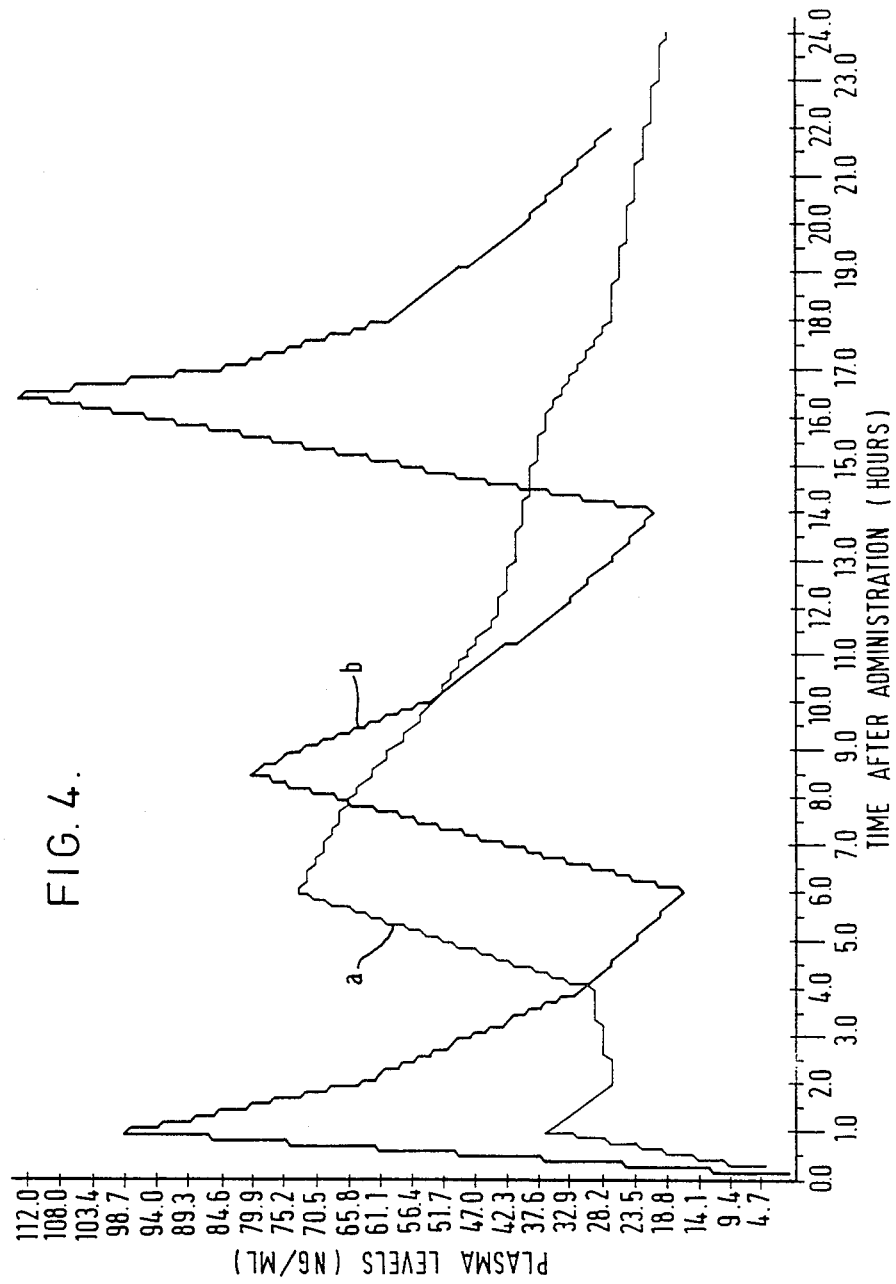
FIG. 4 is a graph of plasma levels (ng/ml) of verapamil versus time after administration (hours) for verapamil capsules as prepared in Example 1 (curve a) compared with conventional tablets (curve b)

FIG. 4 is a graph of plasma levels (ng/ml) of verapamil versus time after administration (hours) for a single-dose (240 mg) of verapamil capsules as prepared in Example 1 (curve a) compared with a single-dose (80 mg) of Cordilox tablets (curve b). The graphs of FIG. 4 were drawn from the mean values obtained for eight subjects according to the data listed in Tables 3, 4, 7 and 8.

Figure 5:
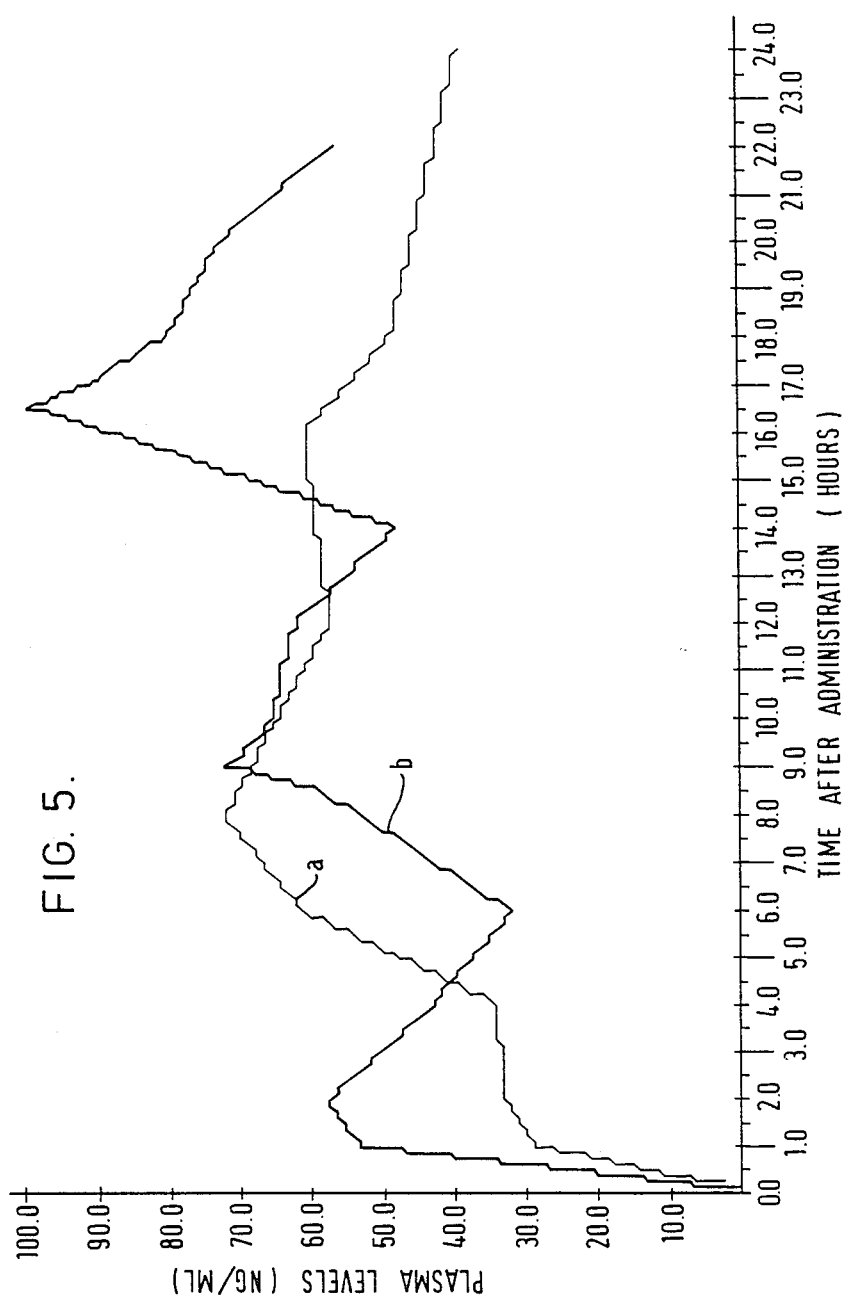
FIG. 5 is a graph of plasma levels (ng/ml) of norverapamil versus time after administration (hours) for verapamil capsules as prepared in Example 1 (curve a) compared with conventional tablets (curve b)

FIG. 5 is a graph of plasma levels (ng/ml) of norverapamil versus time after administration (hours) for a single-dose (240 mg) of verapamil capsules prepared in Example 1 (curve a) compared with a single-dose (80 mg) of Cordilox tablets (curve b). The graphs of FIG. 5 were drawn from the mean values obtained for 8 subjects according to the data listed in Tables 5, 6, 9 and 10.

TABLE 2

VERAPAMIL OF EXAMPLE 2 PERCENTAGE DISSOLUTION

| PH | TIME (HOURS) | | | | | |
|---|---|---|---|---|---|---|
| | 0.00 | 1.00 | 4.00 | 8.00 | 11.00 | 24.00 |
| 3.0 | 0.00 | 17.40 | 23.80 | 40.80 | 60.60 | 99.99 |
| 6.0 | 0.00 | 17.90 | 24.60 | 41.50 | 63.00 | 99.88 |
| 7.5 | 0.00 | 18.90 | 25.80 | 42.40 | 63.10 | 98.99 |
| MEAN | 0.00 | 18.07 | 24.73 | 41.57 | 62.23 | 99.62 |
| ST DEV | 0.00 | 0.76 | 1.01 | 0.80 | 1.42 | 0.55 |
| *CV (%) | 0.00 | 4.23 | 4.07 | 1.93 | 2.27 | 0.55 |

*Coefficient of variation

TABLE 3

VERAPAMIL - EXAMPLE 1 - 240 mg SINGLE-DOSE PLASMA VERAPAMIL LEVELS (ng/ml)

| | HOURS AFTER ADMINISTRATION | | | | | | | | | | | |
|---|---|---|---|---|---|---|---|---|---|---|---|---|
| | 0.00 | 1.00 | 2.00 | 4.00 | 6.00 | 8.00 | 10.00 | 12.00 | 16.00 | 18.00 | 24.00 | 36.00 |
| MEAN | 0.00 | 36.44 | 26.59 | 29.87 | 73.16 | 65.60 | 53.51 | 43.31 | 36.50 | 27.57 | 19.04 | 2.61 |
| ST DEV | 0.00 | 14.66 | 10.92 | 27.80 | 69.56 | 28.22 | 18.23 | 19.32 | 14.18 | 9.43 | 11.87 | 3.57 |
| *CV (%) | 0.00 | 40.22 | 41.09 | 93.08 | 95.09 | 43.02 | 34.06 | 44.61 | 38.84 | 34.20 | 62.33 | 136.50 |
| MAX | 0.00 | 51.40 | 43.40 | 92.50 | 2115.30 | 103.40 | 77.60 | 69.00 | 56.70 | 41.00 | 36.00 | 9.80 |
| MIN | 0.00 | 17.20 | 11.90 | 15.80 | 21.50 | 29.50 | 24.60 | 13.00 | 21.50 | 10.30 | 5.80 | 0.00 |

| MEAN OF CV VALUES AT SAMPLE POINTS | NUMBER OF ZERO BLOOD LEVELS | NUMBER OF POOR ABSORBERS <10% AUC** |
|---|---|---|
| 60.28 | 3 | 0 |

*Coefficient of variation
**Area under the curve

TABLE 4

VERAPAMIL - EXAMPLE 1 - 240 mg AS SINGLE DOSE PHARMACOKINETIC PARAMETERS

| | AUC** | PEAKING TIME T(MAX) | PEAK HEIGHT C(MAX) | C(MAX)/C(MIN) at 24.00 HOURS |
|---|---|---|---|---|
| MEAN | 1057.41 | 8.00 | 90.06 | 5.64 |
| ST DEV | 415.23 | 2.58 | 58.94 | 2.79 |
| *CV (%) | 39.27 | 32.27 | 65.45 | 49.40 |
| BASED ON MEAN BLOOD LEVEL CURVE | | | | |
| MEAN | | 6.00 | 73.16 | 3.84 |

*Coefficient of variation

TABLE 1

VERAPAMIL OF EXAMPLE 1 PERCENTAGE DISSOLUTION

| pH | TIME (HOURS) | | | | | | | | | | | | | |
|---|---|---|---|---|---|---|---|---|---|---|---|---|---|---|
| | 0.00 | 1.00 | 2.00 | 3.00 | 4.00 | 5.00 | 6.00 | 7.00 | 8.00 | 9.00 | 10.00 | 11.00 | 112.00 | 24.00 |
| pH 3.0 | 0.00 | 19.60 | 20.10 | 21.20 | 21.80 | 25.70 | 30.70 | 31.80 | 37.46 | 43.60 | 50.30 | 54.70 | 63.70 | 95.00 |
| pH 6.0 | 0.00 | 19.60 | 20.70 | 22.30 | 23.20 | 25.70 | 28.60 | 33.00 | 39.70 | 44.70 | 50.30 | 54.70 | 62.60 | 94.30 |
| pH 7.5 | 0.00 | 20.10 | 20.70 | 21.80 | 22.90 | 27.90 | 30.20 | 34.10 | 40.80 | 45.80 | 51.40 | 57.00 | 64.80 | 93.20 |
| MEAN | 0.00 | 19.77 | 20.50 | 21.77 | 22.63 | 26.43 | 29.83 | 32.97 | 39.30 | 44.70 | 50.67 | 55.47 | 63.70 | 94. |
| ST DEV | 0.00 | 0.29 | 0.35 | 0.55 | 0.74 | 1.27 | 1.10 | 1.15 | 1.74 | 1.10 | 0.64 | 1.33 | 1.10 | 0.91 |
| *CV (%) | 0.00 | 1.46 | 1.69 | 2.53 | 3.26 | 4.81 | 3.68 | 3.49 | 4.41 | 2.46 | 1.25 | 2.39 | 1.73 | 0.97 |

*Coefficient of variation.

**Area under the curve

TABLE 5

VERAPAMIL - EXAMPLE 1 - 240 mg SINGLE-DOSE PLASMA NORVERAPAMIL LEVELS (ng/ml)

| | HOURS AFTER ADMINISTRATION | | | | | | | | | | | |
|---|---|---|---|---|---|---|---|---|---|---|---|---|
| | 0.00 | 1.00 | 2.00 | 4.00 | 6.00 | 8.00 | 10.00 | 12.00 | 16.00 | 18.00 | 24.00 | 36.00 |
| MEAN | 0.00 | 28.61 | 33.20 | 34.34 | 61.20 | 72.47 | 64.96 | 57.71 | 61.54 | 49.50 | 40.37 | 19.46 |
| ST DEV | 0.00 | 11.03 | 8.44 | 16.50 | 47.33 | 35.89 | 26.22 | 24.48 | 23.14 | 15.50 | 16.71 | 6.70 |
| *CV (%) | 0.00 | 38.54 | 25.41 | 48.03 | 77.33 | 49.52 | 40.37 | 42.42 | 37.61 | 31.32 | 41.39 | 34.43 |
| MAX | 0.00 | 44.10 | 43.50 | 66.50 | 160.20 | 133.00 | 108.10 | 89.50 | 94.40 | 67.60 | 68.00 | 33.60 |
| MIN | 0.00 | 16.30 | 17.90 | 16.00 | 32.00 | 28.10 | 26.20 | 21.10 | 27.20 | 22.70 | 13.40 | 14.70 |

| MEAN OF CV VALUES | NUMBER OF ZERO | NUMBER OF POOR |

TABLE 5-continued

VERAPAMIL - EXAMPLE 1 - 240 mg SINGLE-DOSE PLASMA NORVERAPAMIL LEVELS (ng/ml)

HOURS AFTER ADMINISTRATION

| | 0.00 | 1.00 | 2.00 | 4.00 | 6.00 | 8.00 | 10.00 | 12.00 | 16.00 | 18.00 | 24.00 | 36.00 |
|---|---|---|---|---|---|---|---|---|---|---|---|---|
| AT SAMPLE POINTS | | | BLOOD LEVELS | | | | | | ABSORBERS <10% AUC** | | | |
| 42.20 | | | 0 | | | | | | 0 | | | |

*Coefficient of variation
**Area under the curve

TABLE 6

VERAPAMIL - EXAMPLE 1 - 240 mg AS SINGLE DOSE PHARMACOKINETIC PARAMETERS

| | AUC** | PEAKING TIME T(MAX) | PEAK HEIGHT C(MAX) | C(MAX)/ C(MIN) at 24.00 HOURS |
|---|---|---|---|---|
| MEAN | 1580.21 | 9.43 | 83.89 | 2.13 |
| ST DEV | 567.88 | 3.60 | 40.34 | 0.58 |
| *CV (%) | 35.94 | 38.17 | 48.09 | 27.09 |
| BASED ON MEAN BLOOD LEVEL CURVE | | | | |
| MEAN | | 8.00 | 72.47 | 1.80 |

*Coefficient of variation
**Area under the curve

TABLE 7

VERAPAMIL - CORDILOX 80 mg PLASMA VERAPAMIL LEVELS (ng/ml)

HOURS AFTER ADMINISTRATION

| | 0.00 | 1.00 | 2.00 | 4.00 | 6.00 | 8.50 | 9.00 | 10.00 | 12.00 | 14.00 | 16.50 | 17.00 | 18.00 | 20.00 | 22.00 |
|---|---|---|---|---|---|---|---|---|---|---|---|---|---|---|---|
| MEAN | 0.00 | 98.13 | 64.97 | 31.14 | 17.01 | 79.83 | 73.23 | 54.24 | 34.13 | 20.91 | 113.97 | 84.43 | 60.14 | 39.87 | 27.43 |
| ST DEV | 0.00 | 64.43 | 25.12 | 13.86 | 7.25 | 49.10 | 32.25 | 23.64 | 13.72 | 8.44 | 57.81 | 33.24 | 25.77 | 12.32 | 10.01 |
| CV (%) | 0.00 | 65.66 | 38.66 | 44.51 | 42.60 | 61.50 | 44.04 | 43.59 | 40.21 | 40.37 | 50.73 | 39.38 | 42.85 | 30.89 | 36.50 |
| MAX | 0.00 | 202.30 | 111.20 | 53.40 | 26.30 | 165.70 | 119.80 | 94.80 | 47.60 | 30.70 | 219.90 | 135.20 | 104.70 | 62.00 | 42.80 |
| MIN | 0.00 | 41.80 | 37.40 | 15.60 | 8.90 | 21.10 | 39.10 | 24.60 | 13.50 | 8.20 | 45.60 | 36.40 | 26.80 | 23.50 | 15.40 |

| MEAN OF CV VALUES AT SAMPLE POINTS | NUMBER OF ZERO BLOOD LEVELS | NUMBER OF POOR ABSORBERS <10% AUC** |
|---|---|---|
| 44.39 | 0 | 0 |

TABLE 8

VERAPAMIL - CORDILOX 80 mg PHARMACOKINETIC PARAMETERS

| | AUC** | PEAKING TIME T(MAX) | PEAK HEIGHT C(MAX) | C(MAX)/ C(MIN) at 22.00 HOURS |
|---|---|---|---|---|
| MEAN | 1099.16 | 0.64 | 123.64 | 4.51 |
| ST DEV | 456.41 | 0.24 | 54.52 | 0.95 |
| *CV (%) | 41.52 | 37.95 | 44.09 | 21.04 |
| BASED ON MEAN BLOOD LEVEL CURVE | | | | |
| MEAN | | 0.50 | 113.97 | 4.16 |

*Coefficient of variation
**Area under the curve

TABLE 9

VERAPAMIL - CORDILOX 80 mg PLASMA NORVERAPAMIL LEVELS

HOURS AFTER ADMINISTRATION

| | 0.00 | 1.00 | 2.00 | 4.00 | 6.00 | 8.50 | 9.00 | 10.00 | 12.00 | 14.00 | 16.50 | 17.00 | 18.00 | 20.00 | 22.00 |
|---|---|---|---|---|---|---|---|---|---|---|---|---|---|---|---|
| MEAN | 0.00 | 53.26 | 58.11 | 43.80 | 32.43 | 58.84 | 71.94 | 65.64 | 62.56 | 48.83 | 99.70 | 92.77 | 81.16 | 73.66 | 58.11 |
| ST DEV | 0.00 | 25.10 | 20.18 | 15.73 | 11.42 | 39.87 | 28.10 | 22.53 | 20.89 | 17.14 | 27.00 | 30.99 | 35.28 | 21.06 | 18.09 |
| CV (%) | 0.00 | 47.14 | 34.73 | 35.92 | 35.20 | 67.76 | 39.06 | 34.33 | 33.39 | 35.11 | 27.08 | 33.40 | 43.48 | 28.60 | 31.12 |
| MAX | 0.00 | 87.30 | 81.00 | 70.40 | 49.90 | 133.30 | 108.60 | 98.50 | 92.40 | 73.40 | 143.10 | 131.70 | 132.70 | 97.90 | 87.80 |
| MIN | 0.00 | 26.30 | 33.20 | 21.80 | 16.10 | 6.40 | 38.90 | 31.40 | 27.50 | 22.80 | 64.80 | 40.00 | 39.80 | 37.50 | 32.50 |

| MEAN OF CV VALUES AT SAMPLE POINTS | NUMBER OF ZERO BLOOD LEVELS | NUMBER OF POOR ABSORBERS <10% AUC** |
|---|---|---|
| 37.59 | 0 | 0 |

TABLE 10

VERAPAMIL - CORDILOX 80 mg PHARMACOKINETIC PARAMETERS

| | AUC** | PEAKING TIME T(MAX) | PEAK HEIGHT C(MAX) | C(MAX)/ C(MIN) at 22.00 HOURS |
|---|---|---|---|---|
| MEAN | 1322.95 | 0.64 | 101.09 | 1.77 |
| ST DEV | 443.34 | 0.24 | 27.26 | 0.22 |
| *CV (%) | 33.51 | 37.95 | 26.97 | 12.54 |
| BASED ON MEAN BLOOD LEVEL CURVE | | | | |
| MEAN | | 0.50 | 99.70 | 1.72 |

*Coefficient of variation
**Area under the curve

PHARMACOLOGICAL DATA FOR THE VERAPAMIL FORMULATION PREPARED IN EXAMPLE 2

As will be observed from the data given in Tables 11-16, peak plasma verapamil levels following single-dose administration of the verapamil preparation prepared in Example 2 (240 mg; in capsule form) (83.8 ng/ml) were not significantly different from peak plasma verapamil levels for a single-dose (80 mg) of Cordilox tablets (78.8 ng/ml). As will be observed from the data given in Tables 1-22 peak plasma norverapamil levels were, however, higher with the verapamil formulation of Example 2 (69.6 ng/ml) relative to Cordilox tablets (52.7 ng/ml).

Figure 6:
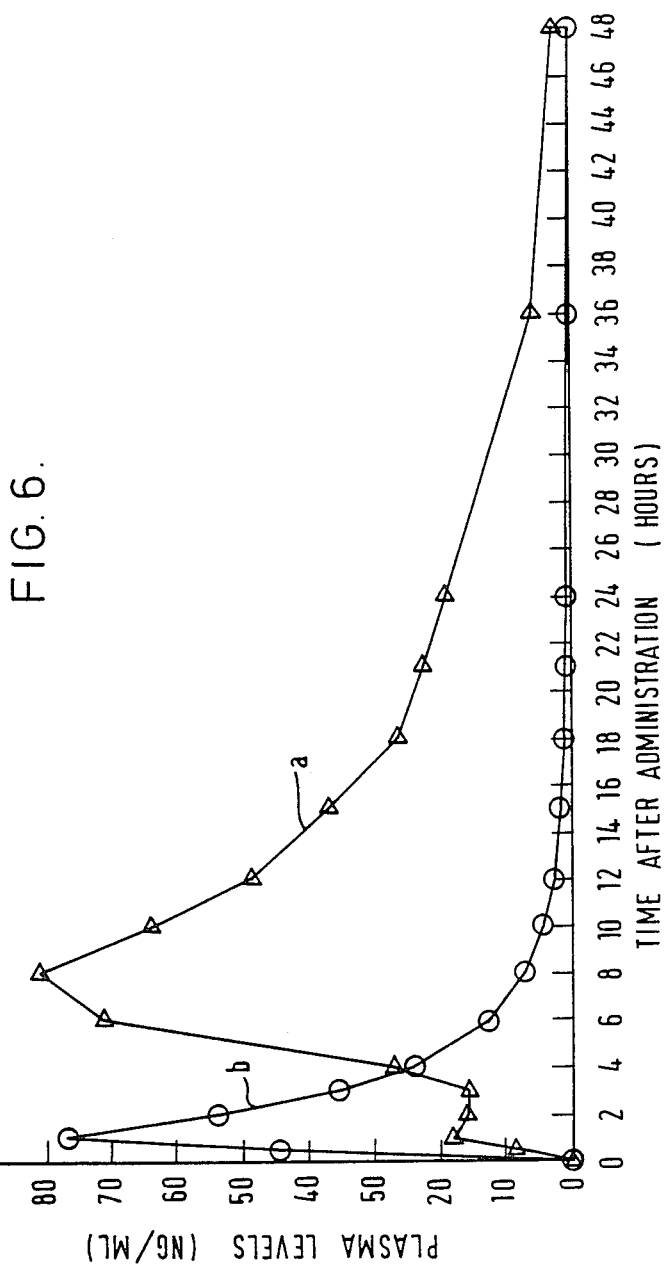
FIG. 6 is a graph of plasma levels (ng/ml) of verapamil versus time after administration (hours) for verapamil capsules as prepared in Example 2 (curve a) compared with conventional tablets (curve b)

FIG. 6 is a graph of plasma levels (ng/ml) of verapamil versus time after administration (hours) for a single-dose (240 mg) of verapamil capsules prepared from a blend of pellets as prepared in Example 2 (curve a) compared with a single dose (80 mg) of Cordilox tablets (curve b). The graphs of FIG. 6 were drawn from the mean values obtained for 22 subjects according to the data listed in Tables 11-16.

Figure 7:
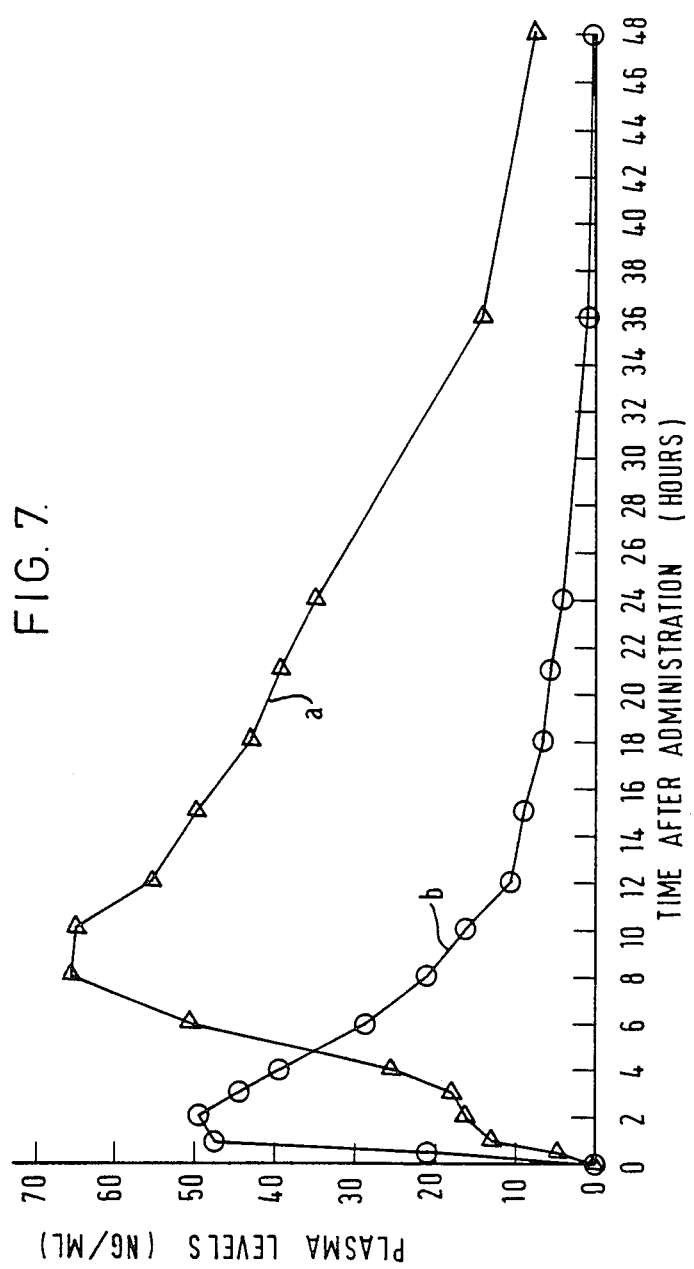
FIG. 7 is a graph of plasma levels (ng/ml) of norverapamil versus time after administration (hours) for verapamil capsules as prepared in Example 2 (curve a) compared with conventional tablets (curve b)

FIG. 7 is a graph of plasma levels (ng/ml) of norverapamil versus time after administration (hours) for a single-dose (240 mg) of verapamil capsules prepared from a blend of pellets as prepared in Example 2 (curve a) compared with a single-dose (80 mg) of Cordilox tablets (curve b). The graphs of FIG. 7 were drawn from the mean values obtained for 22 subjects according to the data listed in Tables 17-22.

Results of steady-state studies performed at day 9 of administration for the blend of tablets prepared in Example 2 and Cordilox tablets are presented in Tables 23-34. Steady-state peak plasma verapamil and norverapamil levels for the verapamil capsules prepared from a blend of pellets as prepared in Example 2 (240 mg) (117.6 ng/ml and 112.8 ng/ml, respectively) were significantly lower than those of Cordilox tablets (80 mg) (172.2 ng/ml and 140.0 ng/ml, respectively).

The verapamil formulation of Example 2 showed markedly delayed single-dose peaking times based both on verapamil (7.6 hours) and norverapamil (9.4 hours) levels compared with Cordilox tablets (1.1 hours and 1.9 hours, respectively). The verapamil and norverapamil peak to 24-hour trough fluctuations of the verapamil formulation of Example 2, (4.8 and 2.1, respectively) were significantly lower than that of the peak to 8-hour trough Cordilox values (11.6 and 2.6, respectively).

The verapamil formulation of Example 2 showed significantly delayed peaking times based both on verapamil (7.7 hours) and norverapamil (9.0 hours) levels compared with Cordilox (1.2 hours and 1.8 hours, respectively).

At steady-state the peak to dosing interval trough plasma verapamil fluctuations of the verapamil formulation of Example 2 (3.7) was significantly lower than that of Cordilox (5.1) whereas the norverapamil peak-to-trough fluctuations were not different (1.8 versus 1.9, respectively).

The apparent verapamil and norverapamil elimination rates of Cordilox (0.29 $h^{-1}$ and 0.12 $h^{-1}$, respectively) were significantly faster than the corresponding single-dose values for the verapamil formulation of Example 2 (0.08 $h^{-1}$ and 0.06 $h^{-1}$, respectively). Apparent half lives for verapamil and norverapamil were significantly longer with the verapamil formulation of Example 2 (8.88 h and 11.5 h, respectively) than with Cordilox (2.61 h and 7.04 h, respectively). These data are consistent with prolonged absorption for the verapamil formulation of Example 2.

At steady-state the apparent verapamil and norverapamil elimination rates of Cordilox (0.12 $h^{-1}$ and 0.07 $h^{-1}$, respectively) were significantly higher than the corresponding values for the verapamil formulation of Example 2 (0.08 $h^{-1}$ and 0.06 $h^{-1}$, respectively). Apparent half lives for verapamil and norverapamil were significantly longer with the verapamil formulation of Example 2 (9.01 h and 12.37 h, respectively) than with Cordilox (6.38 h and 10.03 h, respectively).

Based on dose-adjusted area under the plasma verapamil concentration-time curve (AUC) (see FIG. 8) the relative bioavailability of the verapamil formulation of Example 2 (1128.5 ng×h/ml) was 134% compared with Cordilox (842.5 ng×h/ml. The dose-adjusted norverapamil AUC (see FIG. 9) indicated that the verapamil formulation of Example 2 (1459.6 ng×h/ml) was 104% bioavailable relative to Cordilox (1400.7 ng×h/ml).

The single-dose coefficient of variation of such parameters as AUC (53.7%), Cmax (55.9%) and the average CV (coefficient of variation) across all the sampling times (124.1%) were relatively high with the Cordilox tablets. The corresponding CV values for the verapamil formulation of Example 2 were lower and indicated a more consistent absorption pattern, for example, AUC (39.0%), Cmax (39.2%) and average over the sampling times (59.0%). As was observed in the single-dose phase, the verapamil formulation of Example 2 was consistently lower in terms of the extent of intersubject variability in the steady-state profile compared with Cordilox. Following Cordilox the CV of the AUC (62.4%), Cmax (61.8%) and the average CV across the sampling times (71.9%) were higher than the corresponding values for the verapamil formulation of Example 2 (AUC, 43.3%; Cmax, 44.8% and sampling times 55.0%).

Figure 8:
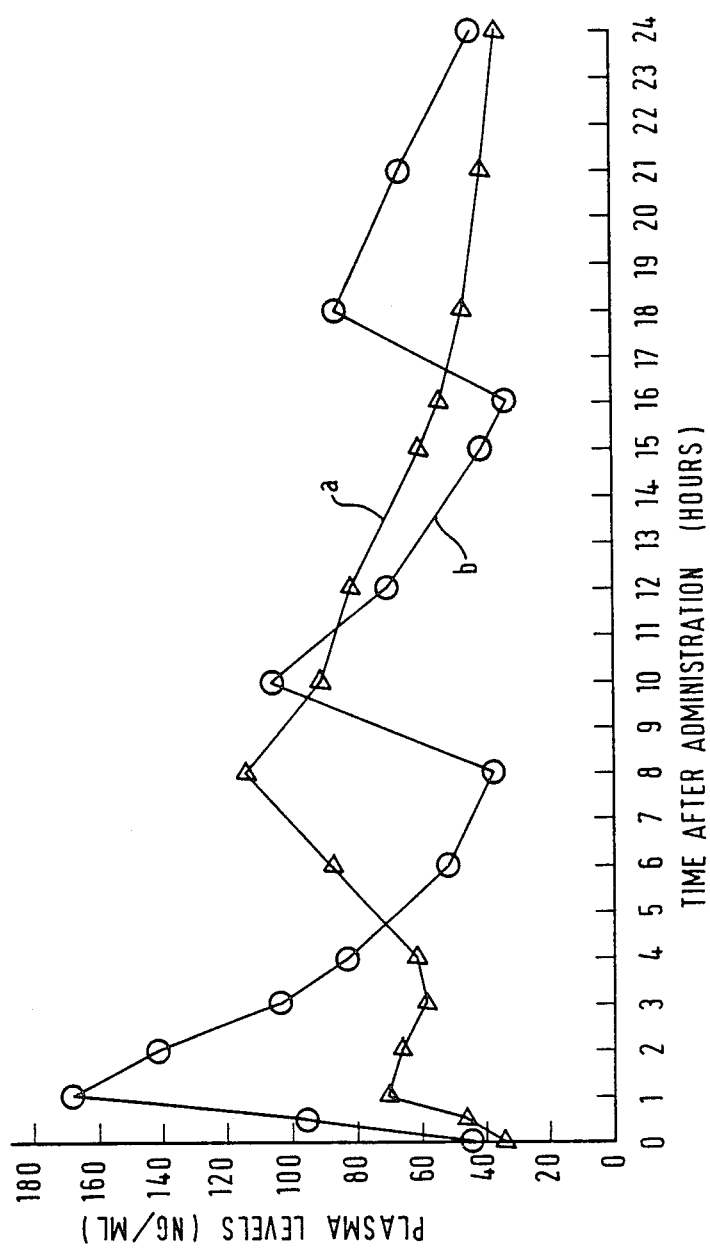
FIG. 8 is a graph of plasma levels (ng/ml) of verapamil at day 9 of administration versus time after administration (hours) for verapamil capsules as prepared in Example 2 (curve a) compared with conventional tablets (curve b)

FIG. 8 is a graph of plasma levels (ng/ml) of verapamil at day 9 of administration versus time after administration (hours) for the verapamil formulation of Example 2 (240 mg) (curve a) compared with Cordilox tablets (80 mg) (curve b). The graphs of FIG. 8 were drawn from the mean values obtained from 22 subjects according to the data listed in Tables 23-28.

FIG. 9 is a graph of plasma levels (ng/m of norverapamil at day 9 of administration versus time after administration (hours) for the verapamil formulation of Example 2 (240 mg) (curve a) compared with Cordilox tablets (80 mg) (curve b). The graphs of FIG. 9 were drawn from the mean values obtained for 22 subjects according to the data listed in Tables 29-34.

TABLE 11

| | VERAPAMIL - EXAMPLE 2 - 240 mg SINGLE-DOSE PLASMA VERAPAMIL LEVELS (ng/ml) | | | | | | | | | | | |
|---|---|---|---|---|---|---|---|---|---|---|---|---|
| | HOURS AFTER ADMINISTRATION | | | | | | | | | | | |
| | 0.00 | 0.50 | 1.00 | 2.00 | 3.00 | 4.00 | 6.00 | 8.00 | 10.00 | 12.00 | 15.00 | 18.00 |
| MEAN | 0.00 | 8.89 | 18.37 | 16.19 | 15.90 | 27.16 | 71.14 | 81.00 | 63.70 | 48.66 | 36.82 | 26.30 |

TABLE 11-continued

VERAPAMIL - EXAMPLE 2 - 240 mg SINGLE-DOSE
PLASMA VERAPAMIL LEVELS (ng/ml)

| | | | | | | | | | | | | |
|---|---|---|---|---|---|---|---|---|---|---|---|---|
| ST DEV | 0.00 | 11.37 | 13.82 | 10.50 | 12.26 | 13.79 | 25.39 | 33.30 | 26.06 | 20.56 | 17.06 | 12.00 |
| *CV (%) | 0.00 | 126.59 | 75.23 | 64.84 | 77.06 | 50.77 | 35.70 | 41.10 | 40.91 | 42.26 | 46.34 | 45.65 |
| MAX | 0.00 | 37.50 | 54.20 | 45.70 | 61.70 | 57.50 | 115.90 | 154.20 | 126.90 | 99.80 | 71.30 | 50.90 |
| MIN | 0.00 | 0.00 | 3.10 | 5.40 | 4.70 | 5.10 | 19.50 | 28.00 | 27.00 | 25.70 | 15.90 | 9.30 |

| MEAN OF CV VALUES AT SAMPLE POINTS | NUMBER OF ZERO BLOOD LEVELS | NUMBER OF POOR ABSORBERS <10% AUC** |
|---|---|---|
| 58.96 | 14 | 0 |

| | HOURS AFTER ADMINISTRATION | | | |
|---|---|---|---|---|
| | 21.00 | 24.00 | 36.00 | 48.00 |
| MEAN | 22.45 | 19.07 | 5.73 | 2.60 |
| ST DEV | 9.84 | 8.15 | 3.54 | 2.32 |
| *CV (%) | 43.83 | 42.20 | 61.89 | 89.40 |
| MAX | 45.30 | 41.00 | 12.60 | 8.30 |
| MIN | 8.40 | 7.40 | 0.00 | 0.00 |

| MEAN OF CV VALUES AT SAMPLE POINTS | NUMBER OF ZERO BLOOD LEVELS | NUMBER OF POOR ABSORBERS <10% AUC** |
|---|---|---|
| 58.96 | 14 | 0 |

*Coefficient of variation
** Area under the curve

TABLE 12

VERAPAMIL LEVELS - EXAMPLE 2 - 240 mg
SINGLE-DOSE
PHARMACOKINETIC PARAMETERS

| | AUC 0–48 H | PEAKING TIME T(MAX) | PEAK HEIGHT C(MAX) | C(MAX)/ C/(MIN) at 24.00 HOURS |
|---|---|---|---|---|
| MEAN | 1128.48 | 7.55 | 83.82 | 4.77 |
| ST DEV | 439.83 | 0.86 | 32.87 | 1.97 |
| *CV (%) | 38.98 | 11.37 | 39.22 | 41.26 |
| BASED ON MEAN BLOOD LEVEL CURVE | | | | |
| MEAN | | 8.00 | 81.00 | 4.25 |

*Coefficient of variation
**Area under the curve

TABLE 13

VERAPAMIL LEVELS - EXAMPLE 2 - 240 mg
mg SINGLE-DOSE

| | K EL. | T ½ |
|---|---|---|
| MEAN | 0.06 | 8.88 |
| S.D. | 0.02 | 1.99 |
| *CV (%) | 25.60 | 22.43 |

*Coefficient of variation
**Area under the curve

TABLE 14

VERAPAMIL - CORDILOX - 80 mg SINGLE-DOSE
PLASMA VERAPAMIL LEVELS (ng/ml)

| | HOURS AFTER ADMINISTRATION | | | | | | | | | | | |
|---|---|---|---|---|---|---|---|---|---|---|---|---|
| | 0.00 | 0.50 | 1.00 | 2.00 | 3.00 | 4.00 | 6.00 | 8.00 | 10.00 | 12.00 | 15.00 | 18.00 |
| MEAN | 0.00 | 44.49 | 76.74 | 53.85 | 35.67 | 23.86 | 12.54 | 7.17 | 4.39 | 2.57 | 1.60 | 0.99 |
| ST DEV | 0.00 | 42.18 | 43.50 | 26.16 | 17.83 | 12.16 | 6.27 | 3.94 | 3.17 | 2.03 | 2.02 | 1.32 |
| *CV (%) | 0.00 | 94.82 | 56.69 | 48.57 | 49.98 | 50.94 | 50.05 | 54.95 | 72.27 | 79.07 | 125.83 | 134.29 |
| MAX | 0.00 | 126.40 | 203.10 | 129.10 | 85.40 | 57.60 | 29.80 | 19.00 | 12.60 | 7.60 | 6.40 | 4.50 |
| MIN | 0.00 | 0.00 | 18.50 | 16.70 | 11.10 | 6.10 | 3.00 | 2.40 | 0.00 | 0.00 | 0.00 | 0.00 |

| MEAN OF CV VALUES AT SAMPLE POINTS | NUMBER OF ZERO BLOOD LEVELS | NUMBER OF POOR ABSORBERS <10% AUC** |
|---|---|---|
| 124.10 | 100 | 0 |

| | HOURS AFTER ADMINISTRATION | | | |
|---|---|---|---|---|
| | 21.00 | 24.00 | 36.00 | 48.00 |
| MEAN | 0.84 | 0.63 | 0.45 | 0.10 |
| ST DEV | 1.25 | 1.01 | 1.21 | 0.49 |
| *CV (%) | 149.04 | 159.50 | 266.41 | 469.04 |
| MAX | 3.20 | 4.00 | 4.30 | 2.30 |
| MIN | 0.00 | 0.00 | 0.00 | 0.00 |

| MEAN OF CV VALUES SAMPLE POINTS | NUMBER OF ZERO BLOOD LEVELS | NUMBER OF POOR ABSORBERS <10% AUC** |
|---|---|---|
| 124.10 | 100 | 0 |

*Coefficient of variation
**Area under the curve

TABLE 15

VERAPAMIL LEVELS - CORDILOX 80 mg - SINGLE-DOSE PHARMACOKINETIC PARAMETERS

|        | AUC 0–48 H | PEAKING TIME T(MAX) | PEAK HEIGHT C(MAX) | C(MAX)/C(MIN) at 8.00 HOURS |
|--------|------------|---------------------|--------------------|-----------------------------|
| MEAN   | 280.82     | 1.05                | 78.84              | 11.55                       |
| ST DEV | 150.83     | 0.34                | 44.04              | 3.84                        |
| *CV (%) | 53.71     | 32.70               | 55.86              | 33.26                       |
| BASED ON MEAN BLOOD LEVEL CURVE | | | | |
| MEAN   |            | 1.00                | 76.74              | 10.71                       |

*Coefficient of variation
**Area under the curve

TABLE 16

CORDILOX 80 mg SINGLE-DOSE - VERAPAMIL LEVELS

|         | K EL. | T ½   |
|---------|-------|-------|
| MEAN    | 0.29  | 2.61  |
| S.D.    | 0.08  | 1.04  |
| *CV (%) | 27.81 | 39.93 |

*Coefficient of variation
**Area under the curve

TABLE 17

VERAPAMIL EXAMPLE 2 - 240 mg SINGLE-DOSE PLASMA NORVERAPAMIL LEVELS (ng/ml)

| HOURS AFTER ADMINISTRATION | | | | | | | | | | | | |
|---|---|---|---|---|---|---|---|---|---|---|---|---|
|        | 0.00 | 0.50 | 1.00 | 2.00 | 3.00 | 4.00 | 6.00 | 8.00 | 10.00 | 12.00 | 15.00 | 18.00 |
| MEAN   | 0.00 | 4.90 | 13.22 | 16.48 | 18.15 | 25.67 | 50.80 | 65.53 | 64.86 | 55.24 | 49.73 | 32.92 |
| ST DEV | 0.00 | 5.70 | 8.80 | 6.02 | 5.13 | 8.09 | 12.99 | 15.16 | 15.57 | 12.44 | 13.35 | 13.25 |
| *CV (%) | 0.00 | 116.23 | 66.57 | 36.53 | 28.26 | 31.51 | 25.56 | 23.14 | 24.00 | 22.52 | 26.84 | 30.86 |
| MAX    | 0.00 | 22.10 | 31.80 | 28.70 | 27.50 | 40.40 | 73.60 | 90.00 | 96.80 | 85.10 | 79.20 | 69.00 |
| MIN    | 0.00 | 0.00 | 1.00 | 7.70 | 10.20 | 12.60 | 23.60 | 32.30 | 34.80 | 31.50 | 27.30 | 23.00 |

| MEAN OF CV VALUES AT SAMPLE POINTS | NUMBER OF ZERO BLOOD LEVELS | NUMBER OF POOR ABSORBERS <10% AUC** |
|---|---|---|
| 39.05 | 8 | 0 |

| HOURS AFTER ADMINISTRATION | | | | |
|---|---|---|---|---|
|        | 21.00 | 24.00 | 36.00 | 48.00 |
| MEAN   | 39.24 | 34.85 | 14.19 | 7.71  |
| ST DEV | 12.92 | 10.29 | 5.66  | 3.96  |
| *CV (%) | 32.92 | 29.54 | 39.90 | 51.33 |
| MAX    | 64.00 | 60.70 | 26.00 | 15.50 |
| MIN    | 19.20 | 10.60 | 7.50  | 0.00  |

| MEAN OF CV VALUES AT SAMPLE POINTS | NUMBER OF ZERO BLOOD LEVELS | NUMBER OF POOR ABSORBERS <10% AUC** |
|---|---|---|
| 39.05 | 8 | 0 |

*Coefficient of variation
**Area under the curve

TABLE 18

NORVERAPAMIL LEVELS - CAPSULES OF EXAMPLE 2 - 240 mg SINGLE-DOSE PHARMACOKINETIC PARAMETERS

|        | AUC 0–48 H | PEAKING TIME T(MAX) | PEAK HEIGHT C(MAX) | C(MAX)/C(MIN) at 24.00 HOURS |
|--------|------------|---------------------|--------------------|-------------------------------|
| MEAN   | 1459.55    | 9.41                | 69.60              | 2.11                          |
| ST DEV | 358.00     | 1.92                | 14.61              | 0.62                          |
| *CV (%) | 24.53     | 20.39               | 20.99              | 29.36                         |
| BASED ON MEAN BLOOD LEVEL CURVE | | | | |
| MEAN   |            | 8.00                | 65.53              | 1.88                          |

*Coefficient of variation
**Area under the curve

TABLE 19

NORVERAPAMIL LEVELS - CAPSULES OF EXAMPLE 2 - 240 mg SINGLE-DOSE

|         | K EL. | T ½   |
|---------|-------|-------|
| MEAN    | 0.06  | 11.50 |
| S.D.    | 0.01  | 2.30  |
| *CV (%) | 17.77 | 20.41 |

*Coefficient of variation
**Area under the curve

TABLE 20

VERAPAMIL - CORDILOX 80 mg SINGLE-DOSE PLASMA NORVERAPAMIL LEVELS (ng/ml)

| HOURS AFTER ADMINISTRATION | | | | | | | | | | | | |
|---|---|---|---|---|---|---|---|---|---|---|---|---|
|      | 0.00 | 0.50 | 1.00 | 2.00 | 3.00 | 4.00 | 6.00 | 8.00 | 10.00 | 12.00 | 15.00 | 18.00 |
| MEAN | 0.00 | 21.35 | 47.72 | 49.44 | 44.51 | 39.45 | 28.64 | 21.22 | 16.48 | 10.75 | 9.10 | 6.62 |

TABLE 20-continued

VERAPAMIL - CORDILOX 80 mg SINGLE-DOSE PLASMA NORVERAPAMIL LEVELS (ng/ml)

| ST DEV | 0.00 | 17.12 | 14.84 | 15.04 | 12.30 | 11.63 | 9.61 | 7.35 | 6.41 | 3.26 | 4.11 | 2.73 |
|---|---|---|---|---|---|---|---|---|---|---|---|---|
| *CV (%) | 0.00 | 80.18 | 31.09 | 30.42 | 27.64 | 29.49 | 33.54 | 34.64 | 38.92 | 30.34 | 45.21 | 41.28 |
| MAX | 0.00 | 65.40 | 72.60 | 74.60 | 71.70 | 56.20 | 47.20 | 39.70 | 29.60 | 18.20 | 15.60 | 11.40 |
| MIN | 0.00 | 0.00 | 16.80 | 24.00 | 17.80 | 16.50 | 12.60 | 10.70 | 4.70 | 4.40 | 0.00 | 0.00 |

| MEAN OF CV VALUES AT SAMPLE POINTS | NUMBER OF ZERO BLOOD LEVELS | NUMBER OF POOR ABSORBERS <10% AUC** |
|---|---|---|
| 56.95 | 39 | 0 |

| | HOURS AFTER ADMINISTRATION | | | |
|---|---|---|---|---|
| | 21.00 | 24.00 | 36.00 | 48.00 |
| MEAN | 5.65 | 4.01 | 0.88 | 0.50 |
| ST DEV | 2.94 | 2.89 | 1.09 | 0.92 |
| *CV (%) | 52.13 | 71.96 | 124.62 | 182.83 |
| MAX | 11.60 | 8.30 | 2.60 | 2.80 |
| MIN | 0.00 | 0.00 | 0.00 | 0.00 |

| MEAN OF CV VALUES AT SAMPLE POINTS | NUMBER OF ZERO BLOOD LEVELS | NUMBER OF POOR ABSORBERS <10% AUC** |
|---|---|---|
| 56.95 | 39 | 0 |

*Coefficient of variation
**Area under the curve

TABLE 21

NORVERAPAMIL LEVELS - FROM CORDILOX 80 mg SINGLE-DOSE PHARMACOKINETIC PARAMETERS

| | AUC 0-48 H | PEAKING TIME T(MAX) | PEAK HEIGHT C(MAX) | C(MAX)/C(MIN) at 8.00 HOURS |
|---|---|---|---|---|
| MEAN | 466.90 | 1.86 | 52.74 | 2.57 |
| ST DEV | 141.45 | 0.89 | 14.30 | 0.47 |
| *CV (%) | 30.30 | 47.69 | 27.12 | 18.12 |
| BASED ON MEAN BLOOD LEVEL CURVE | | | | |
| MEAN | | 2.00 | 49.44 | 2.33 |

*Coefficient of variation
**Area under the curve

TABLE 22

CORDILOX 80 mg SINGLE-DOSE - NORVERAPAMIL LEVELS

| | K EL. | T ½ |
|---|---|---|
| MEAN | 0.12 | 7.04 |
| S.D. | 0.05 | 2.83 |
| *CV (%) | 40.77 | 40.16 |

*Coefficient of variation
**Area under the curve

TABLE 23

VERAPAMIL - EXAMPLE 2 - 240 mg SINGLE-DOSE PLASMA VERAPAMIL LEVELS (ng/ml)

| | HOURS AFTER ADMINISTRATION | | | | | | | | | | | |
|---|---|---|---|---|---|---|---|---|---|---|---|---|
| | 0.00 | 0.00 | 0.50 | 1.00 | 2.00 | 3.00 | 4.00 | 6.00 | 8.00 | 10.00 | 12.00 | 15.00 |
| MEAN | 0.00 | 34.77 | 46.50 | 70.85 | 66.47 | 58.87 | 61.68 | 87.08 | 113.35 | 90.80 | 81.23 | 59.49 |
| ST DEV | 0.00 | 21.19 | 31.53 | 38.82 | 36.12 | 30.04 | 30.42 | 36.45 | 52.25 | 33.43 | 38.44 | 29.38 |
| *CV (%) | 0.00 | 60.93 | 67.80 | 54.80 | 54.34 | 51.03 | 49.32 | 41.86 | 46.10 | 36.94 | 47.32 | 49.39 |
| MAX | 0.00 | 95.60 | 121.10 | 195.10 | 158.50 | 143.00 | 135.80 | 160.30 | 250.20 | 158.30 | 190.50 | 143.80 |
| MIN | 0.00 | 16.20 | 17.30 | 31.50 | 27.80 | 28.30 | 27.40 | 36.60 | 48.80 | 45.90 | 37.50 | 28.10 |

| MEAN OF CV VALUES AT SAMPLE POINTS | NUMBER OF ZERO BLOOD LEVELS | NUMBER OF POOR ABSORBERS <10% AUC** |
|---|---|---|
| 55.04 | 1 | 0 |

| | HOURS AFTER ADMINISTRATION | | | | | |
|---|---|---|---|---|---|---|
| | 16.00 | 18.00 | 21.00 | 24.00 | 36.00 | 48.00 |
| MEAN | 53.17 | 45.89 | 39.80 | 34.84 | 12.65 | 5.65 |
| ST DEV | 26.99 | 22.03 | 20.01 | 20.09 | 10.03 | 5.07 |
| *CV (%) | 50.76 | 48.02 | 50.27 | 57.67 | 79.35 | 89.73 |
| MAX | 122.00 | 100.20 | 94.00 | 92.90 | 45.50 | 21.40 |
| MIN | 22.40 | 19.20 | 16.90 | 16.00 | 4.20 | 0.00 |

| MEAN OF CV VALUES AT SAMPLE POINTS | NUMBER OF ZERO BLOOD LEVELS | NUMBER OF POOR ABSORBERS <10% AUC** |
|---|---|---|

TABLE 23-continued

VERAPAMIL - EXAMPLE 2 - 240 mg SINGLE-DOSE
PLASMA VERAPAMIL LEVELS (ng/ml)

| HOURS AFTER ADMINISTRATION | | |
|---|---|---|
| 55.04 | 1 | 0 |

*Coefficient of variation
**Area under the curve

TABLE 24

VERAPAMIL LEVELS - EXAMPLE 2 - 240 mg SINGLE-DOSE
PHARMACOKINETIC PARAMETERS

| | AUC 0-24 H | PEAKING TIME T(MAX) | PEAK HEIGHT C(MAX) | C(MAX)/C(MIN) at 24.00 HOURS |
|---|---|---|---|---|
| MEAN | 1572.98 | 7.68 | 117.60 | 3.69 |
| ST DEV | 680.48 | 2.03 | 52.69 | 1.40 |
| *CV (%) | 43.26 | 26.46 | 44.80 | 38.01 |
| BASED ON MEAN BLOOD LEVEL CURVE | | | | |
| MEAN | | 8.00 | 113.35 | 3.26 |

*Coefficient of variation
**Area under the curve

TABLE 25

VERAPAMIL - EXAMPLE 2 - 240 mg SINGLE-DOSE

| | K EL. | T ½ |
|---|---|---|
| MEAN | 0.08 | 9.01 |
| S.D. | 0.02 | 2.24 |
| *CV (%) | 25.70 | 24.91 |

*Coefficient of variation
**Area under the curve

TABLE 26

VERAPAMIL - CORDILOX 80 mg SINGLE-DOSE
PLASMA VERAPAMIL LEVELS (ng/ml)

| | HOURS AFTER ADMINISTRATION | | | | | | | | | | | |
|---|---|---|---|---|---|---|---|---|---|---|---|---|
| | 0.00 | 0.00 | 0.50 | 1.00 | 2.00 | 3.00 | 4.00 | 6.00 | 8.00 | 10.00 | 2.00 | 15.00 |
| MEAN | 0.00 | 44.91 | 95.75 | 168.12 | 140.81 | 103.51 | 82.70 | 51.60 | 37.39 | 104.94 | 70.33 | 40.25 |
| ST DEV | 0.00 | 32.20 | 76.09 | 109.14 | 82.86 | 52.61 | 51.74 | 36.92 | 30.51 | 68.44 | 45.90 | 30.78 |
| *CV (%) | 0.00 | 71.70 | 79.47 | 64.92 | 58.84 | 50.83 | 62.57 | 71.55 | 81.60 | 65.22 | 65.27 | 76.47 |
| MAX | 0.00 | 161.60 | 361.30 | 543.40 | 441.70 | 284.40 | 266.10 | 193.10 | 154.70 | 327.80 | 231.50 | 149.20 |
| MIN | 0.00 | 18.30 | 19.80 | 66.30 | 72.80 | 48.00 | 33.10 | 22.20 | 12.60 | 33.40 | 27.80 | 13.20 |

| MEAN OF CV VALUES AT SAMPLE POINTS | NUMBER OF ZERO BLOOD LEVELS | NUMBER OF POOR ABSORBERS <10% AUC** |
|---|---|---|
| 71.94 | 2 | 0 |

| | HOURS AFTER ADMINISTRATION | | | | | |
|---|---|---|---|---|---|---|
| | 16.00 | 18.00 | 21.00 | 24.00 | 36.00 | 48.00 |
| MEAN | 32.45 | 85.48 | 64.70 | 42.73 | 9.59 | 4.17 |
| ST DEV | 28.11 | 50.92 | 50.53 | 30.51 | 8.18 | 3.90 |
| *CV (%) | 86.60 | 59.57 | 78.09 | 71.42 | 85.34 | 93.46 |
| MAX | 139.90 | 211.60 | 263.20 | 157.60 | 39.70 | 14.20 |
| MIN | 10.80 | 23.40 | 25.10 | 17.30 | 2.40 | 0.00 |

| MEAN OF CV VALUES AT SAMPLE POINTS | NUMBER OF BLOOD LEVELS | NUMBER OF POOR ABSORBERS <10% AUC** |
|---|---|---|
| 71.94 | 2 | 0 |

*Coefficient of variation
**Area under the curve

TABLE 27

VERAPAMIL LEVELS - CORDILOX 80 mg SINGLE-DOSE
PHARMACOKINETIC PARAMETERS

| | AUC-SS 0-8H | PEAKING TIME T(MAX) | PEAK HEIGHT C(MAX) | C(MAX)/ C(MIN) at 8.00 HOURS |
|---|---|---|---|---|
| MEAN | 694.15 | 1.16 | 172.23 | 5.07 |
| ST DEV | 433.20 | 0.42 | 106.38 | 1.23 |
| *CV (%) | 62.41 | 36.18 | 61.77 | 24.35 |
| BASED ON MEAN BLOOD LEVEL CURVE | | | | |
| MEAN | | 1.00 | 168.12 | 4.50 |

*Coefficient of variation
**Area under the curve

TABLE 28

CORDILOX 80 mg DAY 9 VERAPAMIL LEVELS

| | K EL. | T ½ |
|---|---|---|
| MEAN | 0.12 | 6.38 |
| S.D. | 0.03 | 1.67 |
| *CV (%) | 25.11 | 26.13 |

*Coefficient of variation
**Area under the curve

TABLE 29

VERAPAMIL-EXAMPLE 2-240 mg SINGLE-DOSE PLASMA NORVERAPAMIL LEVELS (ng/ml)

| | HOURS AFTER ADMINISTRATION | | | | | | | | | | | |
|---|---|---|---|---|---|---|---|---|---|---|---|---|
| | 0.00 | 0.00 | 0.50 | 1.00 | 2.00 | 3.00 | 4.00 | 6.00 | 8.00 | 10.00 | 12.00 | 15.00 |
| MEAN | 0.00 | 57.80 | 63.72 | 73.96 | 80.21 | 78.18 | 83.03 | 90.17 | 108.27 | 98.58 | 95.36 | 87.16 |
| ST DEV | 0.00 | 22.85 | 25.06 | 24.38 | 26.44 | 23.41 | 24.41 | 24.50 | 34.77 | 24.78 | 26.49 | 27.62 |
| *CV (%) | 0.00 | 39.53 | 39.33 | 32.97 | 32.97 | 29.95 | 30.01 | 27.17 | 32.11 | 25.13 | 27.78 | 31.68 |
| MAX | 0.00 | 120.90 | 117.10 | 127.00 | 129.80 | 124.30 | 131.70 | 126.90 | 221.40 | 162.50 | 143.20 | 145.80 |
| MIN | 0.00 | 30.90 | 35.10 | 43.80 | 43.10 | 40.40 | 40.60 | 52.50 | 47.90 | 57.50 | 57.00 | 48.70 |

| MEAN OF CV VALUES AT SAMPLE POINTS | NUMBER OF ZERO BLOOD LEVELS | NUMBER OF POOR ABSORBERS <10% AUC** |
|---|---|---|
| 35.14 | 0 | 0 |

| | | HOURS AFTER ADMINISTRATION | | | | | |
|---|---|---|---|---|---|---|---|
| | | 16.00 | 18.00 | 21.00 | 24.00 | 36.00 | 48.00 |
| | MEAN | 79.39 | 71.33 | 66.59 | 61.74 | 27.93 | 18.04 |
| | ST DEV | 25.79 | 23.25 | 23.89 | 22.82 | 13.42 | 11.33 |
| | *CV (%) | 32.49 | 32.60 | 35.88 | 36.96 | 48.05 | 62.79 |
| | MAX | 132.10 | 124.40 | 127.60 | 114.50 | 66.60 | 54.70 |
| | MIN | 41.20 | 37.60 | 35.90 | 28.60 | 12.70 | 7.20 |

| MEAN OF CV VALUES AT SAMPLE POINTS | NUMBER OF BLOOD LEVELS | NUMBER OF POOR ABSORBERS <10% AUC** |
|---|---|---|
| 35.14 | 0 | 0 |

*Coefficient of variation
**Area under the curve

TABLE 30

NORVERAPAMIL LEVELS 240 mg

PHARMACOKINETIC PARAMETERS

| | AUC-SS 0-24H | PEAKING TIME T(MAX) | PEAK HEIGHT C(MAX) | C(MAX)/C(MIN) at 24.00 HOURS |
|---|---|---|---|---|
| MEAN | 1981/23 | 99.02 | 112.84 | 1.91 |
| ST DEV | 552.36 | 3.23 | 33.64 | 0.41 |
| *CV (%) | 27.88 | 35.81 | 29.81 | 21.19 |

BASED ON MEAN BLOOD LEVEL CURVE

| MEAN | 8.00 | 108.27 | 1.75 |
|---|---|---|---|

*Coefficient of variation
**Area under the curve

TABLE 31

CAPSULES OF EXAMPLE 2 - 240 mg DAY 9 NORVERAPAMIL LEVELS

| | K EL. | T ½ |
|---|---|---|
| MEAN | 0.06 | 12.37 |
| S.D. | 0.01 | 2.41 |
| *CV (%) | 22.72 | 19.44 |

*Coefficient of variation
**Area under the curve

TABLE 32

VERAPAMIL - CORDILOX - 80 mg - DAY 9 PLASMA NORVERAPAMIL LEVELS (ng/ml)

| | HOURS AFTER ADMINISTRATION | | | | | | | | | | | |
|---|---|---|---|---|---|---|---|---|---|---|---|---|
| | 0.00 | 0.00 | 0.50 | 1.00 | 2.00 | 3.00 | 4.00 | 6.00 | 8.00 | 10.00 | 12.00 | 15.00 |
| MEAN | 0.00 | 79.51 | 97.19 | 130.45 | 135.93 | 123.98 | 119.61 | 100.04 | 82.98 | 106.90 | 103.49 | 82.64 |
| ST DEV | 0.00 | 32.12 | 38.88 | 48.09 | 44.05 | 36.32 | 41.72 | 34.55 | 33.95 | 34.68 | 37.59 | 38.64 |
| *CV (%) | 0.00 | 40.40 | 40.01 | 36.86 | 32.41 | 29.30 | 34.88 | 34.54 | 40.92 | 32.45 | 36.32 | 46.75 |
| MAX | 0.00 | 191.80 | 206.20 | 275.90 | 274.80 | 223.30 | 253.20 | 203.30 | 181.30 | 180.30 | 216.40 | 197.20 |
| MIN | 0.00 | 45.70 | 47.00 | 65.00 | 85.60 | 77.90 | 75.80 | 59.40 | 44.30 | 57.30 | 61.60 | 46.10 |

| MEAN OF CV VALUES AT SAMPLE POINTS | NUMBER OF ZERO BLOOD LEVELS | NUMBER OF POOR ABSORBERS <10% AUC** |
|---|---|---|
| 41.62 | 0 | 0 |

| | | HOURS AFTER ADMINISTRATION | | | | | |
|---|---|---|---|---|---|---|---|
| | | 16.00 | 18.00 | 21.00 | 24.00 | 36.00 | 48.00 |
| | MEAN | 74.58 | 97.67 | 96.85 | 81.58 | 29.89 | 16.41 |
| | ST DEV | 35.29 | 38.93 | 45.88 | 34.13 | 18.78 | 10.42 |
| | *CV (%) | 47.32 | 39.86 | 47.37 | 41.84 | 62.85 | 63.49 |
| | MAX | 185.20 | 174.50 | 261.50 | 191.00 | 91.00 | 46.50 |
| | MIN | 40.90 | 49.20 | 47.70 | 47.60 | 13.00 | 7.20 |

| MEAN OF CV VALUES AT SAMPLE POINTS | NUMBER OF BLOOD LEVELS | NUMBER OF POOR ABSORBERS <10% AUC** |
|---|---|---|
| 41.62 | 0 | 0 |

*Coefficient of variation
**Area under the curve

TABLE 33

NORVERAPAMIL LEVELS - CORDILOX 80 mg

PHARMACOKINETIC PARAMETERS

| | PEAKING | PEAK | C(MAX)/ |

TABLE 33-continued
NORVERAPAMIL LEVELS - CORDILOX 80 mg

|  | AUC-SS 0-8H | TIME T(MAX) | HEIGHT C(MAX) | C(MIN) at 8.00 HOURS |
|---|---|---|---|---|
| MEAN | 888.69 | 1.77 | 140.00 | 1.76 |
| ST DEV | 298.95 | 0.75 | 45.22 | 0.31 |
| *CV (%) | 33.64 | 42.40 | 32.30 | 17.67 |
| BASED ON MEAN BLOOD LEVEL CURVE | | | | |
| MEAN |  | 2.00 | 135.93 | 1.64 |

*Coefficient of variation
**Area under the curve

TABLE 34
CORDILOX 240 mg DAY 9 NORVERAPAMIL LEVELS

|  | K EL. | T ½ |
|---|---|---|
| MEAN | 0.07 | 10.03 |
| S.D. | 0.01 | 1.94 |
| *CV (%) | 16.31 | 19.30 |

*Coefficient of variation
**Area under the curve

The results of the bioavailability studies above show that the controlled absorption verapamil formulation according to the present invention is an effective once daily form of verapamil, as demonstrated by good bioavailability, delayed peaking time and prolonged effective plasma levels through to 24 hours after administration.

The formulation of Example 2 was tested in in vivo clinical trials in subjects suffering from mild to moderate hypertension. A total group of 118 patients were enrolled in these studies, medically diagnosed as suffering from mild to moderate hypertension and exhibiting associated raised blood pressure values. The subjects were titrated on various dosage strengths of the formulation of Example 2 in order to determine the optimum dosage for reduction and control of blood pressure in each individual patient. It will be observed from Table 35 that 39 subjects were successfully titrated at 120 mg once-daily, 55 subjects were successfully titrated at 240 mg and 24 subjects were successfully titrated at a dose greater than 240 mg once-daily (which was 360 mg or 480 mg). All subjects were then given the titrated dose in a once-daily regimen and blood pressured monitored for 1 month's therapy. It can be seen from Table 35 that blood pressure was effectively reduced and controlled for 1 month by administration of a once-daily dose of the formulation of Example 2. This reduction averaged 22/16 mmHg when compared to baseline values.

Additionally, 61 subjects who were similarly titrated to optimum once-daily dosage levels of the formulation of Example 2 were given this titrated dose on a once-daily regimen for 3 months and blood pressure was monitored over this period. It can be seen from Table 36 that blood pressure was effectively reduced and controlled for 3 months by administration of a once-daily dose of the formulation of Example 2, and it is further demonstrated that this formulation is effective in the long-term control of blood pressure in mild to moderate hypertension, in a once-daily dosage regimen. This reduction averaged 24/18 mmHg when compared to baseline values.

TABLE 35
COMBINED DATA - ONE MONTH PLATEAU DOSAGE THERAPY VERAPAMIL CAPSULES OF EXAMPLE 2 - HYPERTENSION BP VALUES

|  | Mean Supine Systolic/ Diastolic BP (mm Hg) | | |
|---|---|---|---|
| Dosage Groups | Baseline | Completed Titration | 1 Month Therapy |
| 120 mg (N = 39) | 172/102 | 150/87 | 150/87 |
| 240 mg (N = 55) | 168/102 | 148/87 | 146/86 |
| >240 mg (N = 24) | 179/107 | 158/90 | 157/88 |
| All groups (N = 118) | 172/103 | 151/88 | 150/87 |

TABLE 36
COMBINED DATA - 3 MONTH PLATEAU DOSAGE THERAPY VERAPAMIL CAPSULES OF EXAMPLE 2 - HYPERTENSION BP VALUES

|  | Mean Supine Systolic/ Diastolic BP (mm Hg) | | | |
|---|---|---|---|---|
| Dosage Groups | Baseline | Completed Titration | 1 Month Therapy | 3 Month Therapy |
| 120 mg (N = 28) | 170/102 | 151/87 | 149/86 | 149/84 |
| 240 mg (N = 23) | 171/104 | 145/87 | 145/87 | 143/88 |
| >240 mg (N = 10) | 186/188 | 162/89 | 159/87 | 162/87 |
| All groups (N = 61) | 173/104 | 151/87 | 149/87 | 149/86 |

The formulation of Example 2 was also tested in vivo in a randomized, double blind, placebo controlled cross-over study in a determination of efficacy in the treatment of chronic stable angina pectoris. A total of 18 subjects completed this trial. The formulation of Example 2 was administered as a single daily dose of 360 mg to all patients. Assessment was by computer-assisted multistage exercise testing, performed 22-24 hours after drug administration, and by 24 hour ambulatory electrocardiography. Mean exercise time for the subjects at the placebo dosing stage was 6.6 minutes. The formulation of Example 2 resulted in a significant increase in mean exercise time, as compared with placebo, of 8.89 minutes, (or an increase of 2.29 minutes, $p<0.001$). This increase in exercise time was sustained during the 4 weeks of therapy. The time to the development of a 1 mm S-T depression (as determined by electrocardiography) was also increased with the formulation of Example 2. Peak S-T depression during exercise was unaltered by therapy with the formulation of Example 2, despite the increased exercise tolerance. All of these effects were observed 22-24 hours after the preceding dose of medication, indicating that satisfactory effect was being achieved throughout the day. In conclusion, the formulation of Example 2 was shown to be satisfactory for the treatment of angina pectoris, in a once-daily dosage regimen.

What we claim is:

1. A controlled absorption verapamil containing pellet formulation for oral administration, said pellet comprising:
   (i) a core of
      (a) a powder mixture containing verapamil or a pharmaceutically acceptable salt thereof and an organic acid selected from the group consisting of adipic acid, ascorbic acid, citric acid, fumaric acid, malic acid, succinic acid and tartaric acid or a mixture thereof, and
      (b) a polymeric material containing a major proportion of a pharmaceutically acceptable water soluble polymer and a minor proportion of a pharmaceutically acceptable water insoluble polymer, said core comprising layers of said powder mixture and said polymeric material superimposed one upon the other and said polymeric material being present in an amount effective to ensure that all of said powder mixture is coated into said core; and (ii) a multi-layer membrane surrounding said core and containing a major proportion of a pharmacuetically acceptable film-forming, water-insoluble polymer and a minor proportion of a pharmaceutically acceptable film-forming, water-soluble polymer;

the ratio of said verapamil to said organic acid in the core, the number of layers in said membrane and the ratio of said water-soluble polymers to said water-insoluble polymers being effective to permit release of said verapamil from said pellet at a rate allowing controlled absorption thereof over a 24 hour period following oral administration, said rate being measured in vivo and having a Tmax between 6 and 16 hours.

2. A pellet formulation according to claim 1, which has a Tmax in vivo between 7 and 10 hours.

3. A controlled absorption verapamil containing pellet formulation for oral administration, said pellet comprising:

(1) a core of
(a) a powder mixture containing verapamil or a pharmaceutically acceptable salt thereof and an organic acid selected from the group consisting of adipic acid, ascorbic acid, citric acid, fumaric acid, malic acid, succinic acid and tartaric acid or a mixture thereof, and
(b) a polymeric material containing a major proportion of a pharamaceutically acceptable water soluble polymer and a minor proportion of a pharamaceutically acceptable water insoluble polymer, said core comprising layers of said powder mixture and said polymeric material superimposed one upon the other and said polymeric material being present in an amount effective to ensure that all of said powder mixture is coated into said core; and (ii) a multi-layer membrane surrounding said core and containing a major proportion of a pharamaceutically acceptable film-forming, water-insoluble polymer and a minor proportion of a pharmaceutically acceptable film-forming, water-soluble polymer;

the ratio of said verapamil to said organic acid in the core, the number of layers in said membrane and the ratio of said water-soluble polymers to said water-insoluble polymers being effective to permit release of said verapamil from said pellet at a rate which is substantially pH independent and which allows controlled absorption thereof over a 24 hour period following oral administration, said rate being measured in vitro as a dissolution rate of said pellet in a potassium chloride medium which, when measured in a basket in a basket assembly according to U.S. Pharmacopoeia XXI at 37° C., substantially corresponds to the following:

(a) from 0 to 25% of the total verapamil is released after one hour of measurement in said assembly;
(b) from 0 to 35% of the total verapamil is released after four hours of measurement in said assembly;
(c) from 30 to 60% of the total verapamil is released after a total of eight hours of measurement in said assembly;
(d) from 50 to 75% of the total verapamil is released after eleven hours of measurement in said assembly; and
(e) not less than 80% of the total verapamil is released after twenty-four hours of measurement in said assembly.

4. A pellet formulation according to claim 1, wherein the verapamil or pharmaceutically acceptable salt thereof and organic acid are present in a ratio of from 1:1 to 10:1.

5. A pellet formulation according to claim 3, wherein the verapamil or pharmaceutically acceptable salt thereof and organic acid are present in a ratio of from 1:1 to 10:1.

6. A pellet formulation according to claim 1, wherein the polymeric material of the core includes a major proportion of a polymer which is freely permeable to verapamil and water.

7. A pellet formulation according to claim 3, wherein the polymeric material of the core includes a major proportion of a polymer which is freely permeable to verapamil and water.

8. A pellet formulation according to claim 6, wherein the polymeric material of the core includes a minor proportion of a polymer which is slightly permeable to verapamil and water.

9. A pellet formulation according to claim 7, wherein the polymeric material of the core includes a minor proportion of a polymer which is slightly permeable to verapamil and water.

10. A pellet formulation according to claim 1, wherein the water soluble polymer is selected from the group consisting of hydroxypropylmethylcellulose and polyvinylpyrrolidone.

11. A pellet formulation according to claim 6, wherein the polymeric material which is freely permeable to verapamil and water comprises a copolymer of acrylic and methacrylic acid esters.

12. A pellet formulation according to claim 7, wherein the polymeric material which is freely permeable to verapamil and water comprises a copolymer of acrylic and methacrylic acid esters.

13. A pellet formulation according to claim 1, wherein the water insoluble polymer is selected from the group consisting of methylcellulose, ethylcellulose, propylcellulose and shellac.

14. A pellet formulation according to claim 8, wherein the polymer which is slightly permeable to verapamil and water comprises a copolymer of acrylic and methacrylic acid esters.

15. A pellet formulation according to claim 9, wherein the polymer which is slightly permeable to verapamil and water comprises a copolymer of acrylic and methacrylic acid esters.

16. A pellet formulation according to claim 1, wherein the verapamil, organic acid and polymeric material are built up on an inert core.

17. A pellet formulation according to claim 3, wherein the verapamil, organic acid and polymeric material are built up on an inert core.

18. A pellet formulation according to claim 16, wherein the inert core is a non-pareil seed having an average diameter of from 0.3 to 0.7 mm.

19. A pellet formulation according to claim 17, wherein the inert core is a non-pareil seed having an average diameter of from 0.3 to 0.7 mm.

20. A pellet formulation according to claim 1, wherein the core includes one or more additional components selected from the group consisting of a lubricant, a dispersing agent and a surfactant.

21. A pellet formulation according to claim 3, wherein the core includes one or more additional components selected from the group consisting of a lubricant, a dispersing agent and a surfactant.

22. A pellet formulation according to claim 1, wherein the water insoluble polymer of the membrane is selected from the group consisting of shellac, cellulose acetate and ethylcellulose.

23. A pellet formulation according to claim 3, wherein the water insoluble polymer of the membrane is selected from the group consisting of shellac, cellulose acetate and ethylcellulose.

24. A pellet formulation according to claim 22, wherein the water soluble polymer of the membrane is selected from the group consisting of polyvinylpyrrolidone, polyvinylalcohol and hydroxypropylmethylcellulose.

25. A pellet formulation according to claim 23, wherein the water soluble polymer of the membrane is selected from the group consisting of polyvinylpyrrolidone, polyvinylalcohol and hydroxypropylmethylcellulose.

26. A pellet formulation according to claim 1, wherein multi-layer membrane is composed of a major proportion of a polymer which is slightly permeable to verapamil and water and a minor proportion of a polymer which is freely permeable to verapamil and water.

27. A pellet formulation according to claim 26, wherein each of the slightly permeable and freely permeable polymers comprises a copolymer of acrylic and methacrylic acid esters having the desired permeability characteristics.

28. A pellet formulation according to claim 1, wherein the multi-layer membrane is composed of a major proportion of a non-porous polymer and a minor proportion of a porous polymer.

29. A pellet formulation according to claim 1, which contains verapamil hydrochloride as the active ingredient.

30. A process for the production of a pellet formulation according to claim 1, which comprises forming a core of verapamil or a pharmaceutically acceptable salt thereof and an organic acid and enclosing the core in a membrane of a film-forming polymer or mixture thereof which permits release of the verapamil or a pharmaceutically acceptable salt thereof in the manner set out in claim 1.

31. A controlled absorption verapamil formulation for oral administration comprising a blend of pellets as defined in claim 1 in admixture with pellets of a rapid release form of verapamil to ensure a rapid attainment of effective therapeutic blood levels of verapamil within one hour following administration, said rapid release pellets comprising pellets as defined in claim 1 without said multi-layer membrane.

32. A controlled absorption verapamil formulation for oral administration comprising a blend of pellets as defined in claim 3 in admixture with pellets of a rapid release form of verapamil to ensure a rapid attainment of effective therapeutic levels of verapamil within one hour following administration, said rapid release pellets comprising pellets as defined in claim 3 without said multi-layer membrane the formulation having a dissolution rate which is substantially pH independent and which when measured in a basket assembly according to U.S. Pharmacopoeia XXI at 37° C. has the following characteristics:
    (a) from 10 to 25% of the total verapamil is released after one hour of measurement in said assembly;
    (b) from 20 to 35% of the total verapamil is released after four hours of measurement in said assembly;
    (c) from 35 to 60% of the total verapamil is released after eight hours of measurement in said assembly;
    (d) from 50 to 75% of the total verapamil is released after eleven hours of measurement in said assembly; and
    (e) not less than 80% of the total verapamil is released after twenty-four hours of measurement in said assembly.

33. A pellet formulation according to claim 31, which contains up to 12.5% by weight of said rapid release form of verapamil.

34. A pellet formulation according to claim 32, which contains up to 12.5% by weight of said rapid release form of verapamil.

35. A capsule or tablet comprising a formulation of pellets according to claim 31.

36. A capsule or tablet comprising a formulation of pellets according to claim 32.

37. A method of treating or controlling blood pressure in a subject suffering from mild to moderate hypertension, comprising administering to said subject on a once per day basis a dose effective to lower the blood pressure of said subject, of a verapamil-containing controlled absorption formulation comprising effective amounts of a first component formulated to provide an effective blood pressure lowering amount of verapamil within one hour following administration and a second component formulated to provide a maximum blood pressure lowering effect within 6 to 16 hours following administration, wherein said formulation contains up to 12.5% by weight of said first component.

38. A method of controlling or preventing angina attacks or reducing the incidence of angina attacks in a subject suffering from angina pectoris, comprising administering to said subject on a once per day basis a dose effective to improve the blood supply and hence increase the oxygen supply in the myocardium of said subject, of a verapamil-containing controlled absorption formulation comprising effective amounts of a first component formulated to provide an amount of verapamil effective to increase the oxygen supply to the myocardium within one hour following administration and a second component formulated to provide a maximum supply of oxygen to the myocardium within 6 to 16 hours following administration, wherein said formulation contains up to 12.5% by weight of said first component.

* * * * *